US011733337B2

(12) United States Patent
Witcomb et al.

(10) Patent No.: US 11,733,337 B2
(45) Date of Patent: Aug. 22, 2023

(54) DEVICE, SYSTEM AND METHOD FOR TRANSFORMING A DIFFUSION-WEIGHTED MAGNETIC RESONANCE IMAGE TO A PATIENT DIFFUSION-WEIGHTED MAGNETIC RESONANCE COORDINATE SPACE

(71) Applicant: SYNAPTIVE MEDICAL INC., Toronto (CA)

(72) Inventors: Neil Jeffrey Witcomb, Toronto (CA); Simon Kenley Alexander, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 894 days.

(21) Appl. No.: 16/451,605

(22) Filed: Jun. 25, 2019

(65) Prior Publication Data
US 2020/0405174 A1    Dec. 31, 2020

(51) Int. Cl.
*A61B 5/055* (2006.01)
*G01R 33/54* (2006.01)
*A61B 5/00* (2006.01)

(52) U.S. Cl.
CPC ............ *A61B 5/055* (2013.01); *A61B 5/0033* (2013.01); *G01R 33/54* (2013.01)

(58) Field of Classification Search
CPC ...... A61B 5/055; A61B 5/0033; G01R 33/54; G01R 33/543; G01R 33/56341; G06T 2207/10092; G06T 3/0068; G06T 3/00; G06T 7/30; G06T 2207/10081; G06T 2207/10088; G06T 2207/10104
See application file for complete search history.

(56) References Cited

U.S. PATENT DOCUMENTS

| | | | |
|---|---|---|---|
| 2015/0010223 A1 | 1/2015 | Sapiro et al. | |
| 2016/0070436 A1* | 3/2016 | Thomas | G06T 19/003 715/771 |

OTHER PUBLICATIONS

Derek L G Hill et al 2001 Phys. Med. Biol. 46 R1 (Year: 2001).*
(Continued)

*Primary Examiner* — Joel Lamprecht
*Assistant Examiner* — Amy Shafqat
(74) *Attorney, Agent, or Firm* — Perry + Currier, Inc.

(57) ABSTRACT

A computing device: compares an anatomical magnetic resonance (MR) image of a patient region and reference anatomical data associated with the region to determine a first transform of a bore anatomical coordinate space of the anatomical MR image to a patient anatomical coordinate space associated with the patient; determines, from the first transform, a second transform of a bore DWMR coordinate space of a DWMR image to a patient DWMR coordinate space associated with the patient, the anatomical and the DWMR images being in respective bore coordinate spaces associated with a bore of an MR device which acquired the anatomical and the DWMR images; transforms, using the second transform, the DWMR image to the patient DWMR coordinate space; and controls a display screen to render the DWMR image, as transformed, according to visual attributes associated with the patient DWMR coordinate space.

16 Claims, 16 Drawing Sheets

(56) References Cited

OTHER PUBLICATIONS

Marami, Bahram, et al. "Motion-robust diffusion-weighted brain MRI reconstruction through slice-level registration-based motion tracking." IEEE transactions on medical imaging 35.10 (2016): 2258-2269.

Bhushan, Chitresh, et al. "Correcting susceptibility-induced distortion in diffusion-weighted MRI using constrained nonrigid registration." Proceedings of the 2012 Asia Pacific Signal and Information Processing Association Annual Summit and Conference. IEEE, 2012.

* cited by examiner

DEVICE, SYSTEM AND METHOD FOR TRANSFORMING A DIFFUSION-WEIGHTED MAGNETIC RESONANCE IMAGE TO A PATIENT DIFFUSION-WEIGHTED MAGNETIC RESONANCE COORDINATE SPACE

FIELD

The specification relates generally to medical imaging, and, in particular, a device, system and method for transforming a diffusion-weighted magnetic resonance image to a patient diffusion-weighted magnetic resonance coordinate space.

BACKGROUND

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimes, and radiation therapy are only a few examples of procedures utilizing imaging guidance in the medical field.

Advanced imaging modalities such as Magnetic Resonance Imaging ("MRI") have led to improved rates and accuracy of detection, diagnosis and staging in several fields of medicine including neurology, where imaging of diseases such as brain cancer, stroke, Intra-Cerebral Hemorrhage ("ICH"), and neurodegenerative diseases, such as Parkinson's and Alzheimer's, are performed. As an imaging modality, MRI enables three-dimensional visualization of tissue with high contrast in soft tissue without the use of ionizing radiation. This modality is often used in conjunction with other modalities such as Ultrasound ("US"), Positron Emission Tomography ("PET") and Computed X-ray Tomography ("CT"), by examining the same tissue using the different physical principals available with each modality. CT is often used to visualize boney structures, and blood vessels when used in conjunction with an intra-venous agent such as an iodinated contrast agent. Vascular visualization may also be acquired by MRI using a contrast agent, such as an intra-venous gadolinium based contrast agent which has pharmaco-kinetic properties that enable visualization of tumors (in some instances), and break-down of the blood brain barrier. These multi-modality solutions may provide varying degrees of contrast between different tissue types, tissue function, and disease states. Imaging modalities may be used in isolation, or in combination to better differentiate and diagnose disease.

Patient positioning is often the most time-consuming aspect of setting up for an imaging study, including MRI studies. For example, it is desirable to align the patient anatomy as much as possible to the imaging device (e.g. scanner) frame of reference, for example aligned with a bore of an MRI device. This is analogous to the way a map is aligned to a compass when way finding in the physical world. However, due to patient comfort and other factors, such as the way external equipment is attached, and/or how a patient is anchored to a scanning bed, alignment of patient anatomy to the imaging device frame of reference is not always possible. In particular, a patient is positioned in their most comfortable position to minimize patient movement during a scan. Even when in an interpretative situation, where a patient may be sedated, optimal positioning may be limited because of a site of a surgery and the way patient was optimized for the surgical position.

However, it is not always possible to provide instructions to the imaging device/scanner on a desirable scan orientation based on the way patient is positioned. Hence, images acquired are generally in a coordinate space associated with a bore of an MRI device. As such processing of such images can be problematic as applications used for such processing generally operate under an assumption that a patient is aligned with the bore of the MRI device. This is especially problematic when diffusion-weighted magnetic resonance (DWMR) images are acquired.

BRIEF DESCRIPTIONS OF THE DRAWINGS

The patent or application file contains at least one drawing executed in color. Copies of this patent or patent application publication with color drawing(s) will be provided by the Office upon request and payment of the necessary fee.

Embodiments will now be described, by way of example only, with reference to the drawings, in which.

Figure 10:
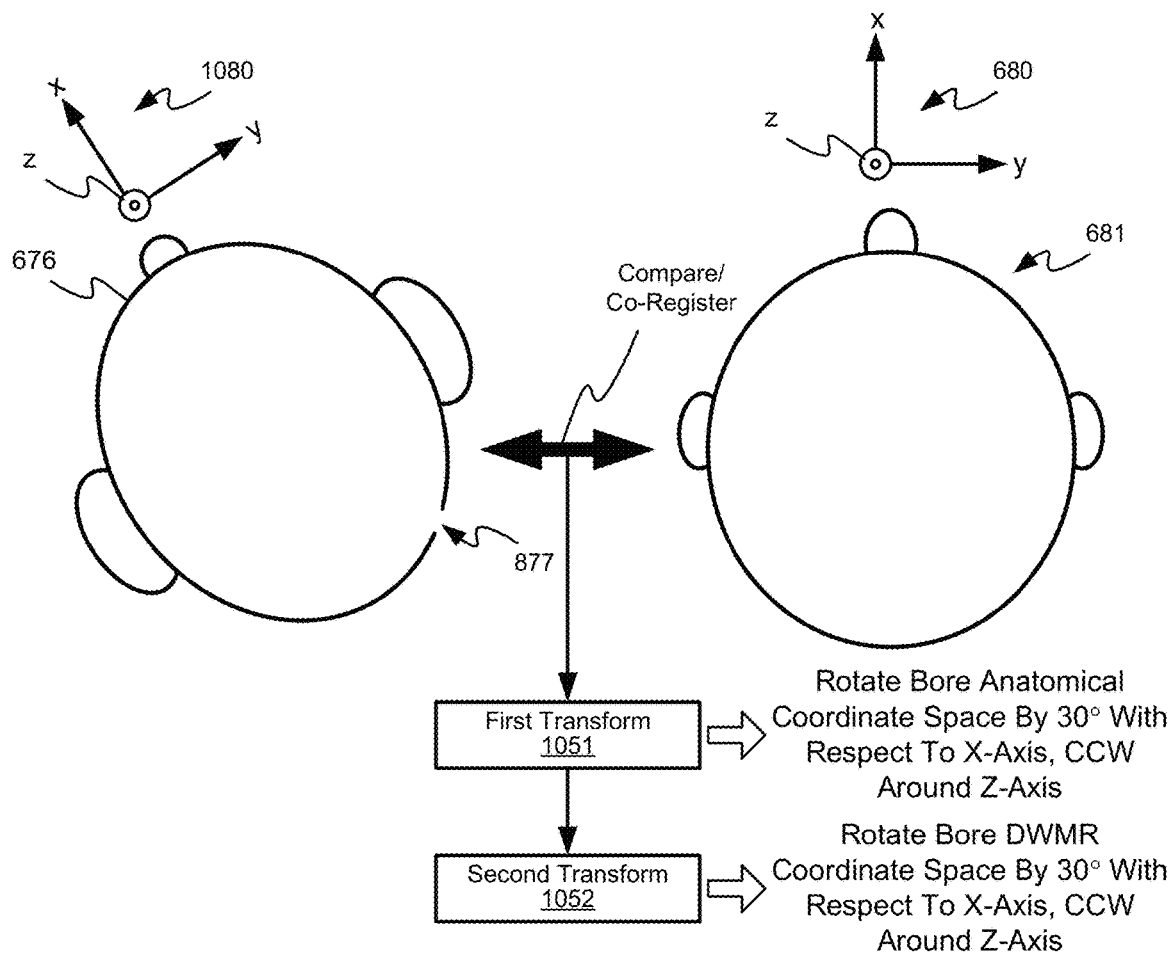

FIG. 10 depicts a determination of a first transform of a bore anatomical coordinate space of an anatomical magnetic resonance image to a patient anatomical coordinate space associated with the patient, and a determination of a second transform of a bore diffusion-weighted magnetic resonance coordinate space of a diffusion-weighted magnetic resonance image to a patient diffusion-weighted magnetic resonance coordinate space associated with the patient, according to non-limiting examples.

Figure 11:
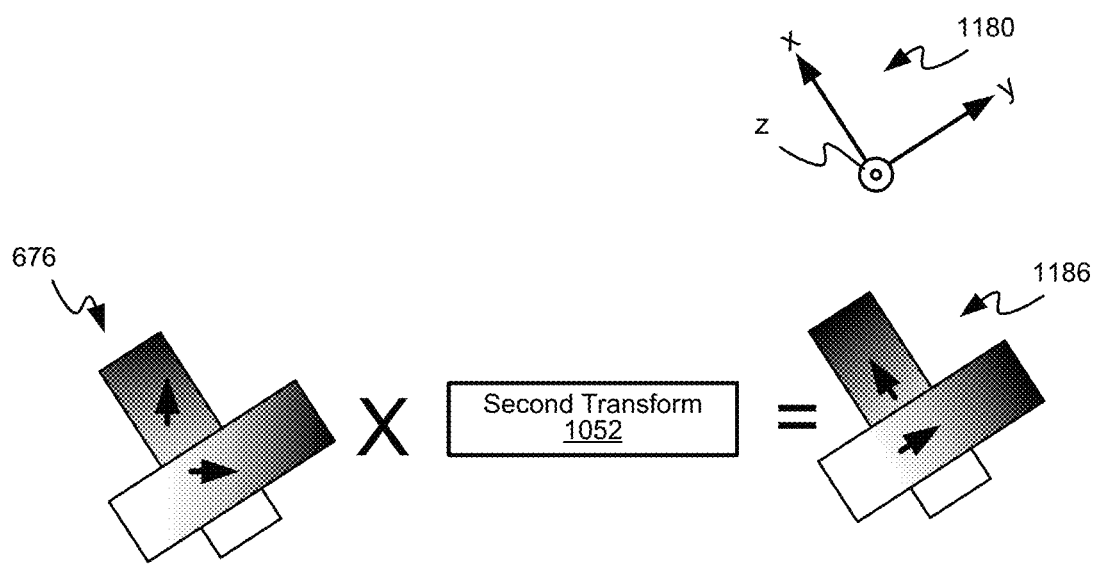

FIG. 11 depicts a transformation, using the second transform, of a diffusion-weighted magnetic resonance image to the patient diffusion-weighted magnetic resonance coordinate space, according to non-limiting examples.

Figure 12:
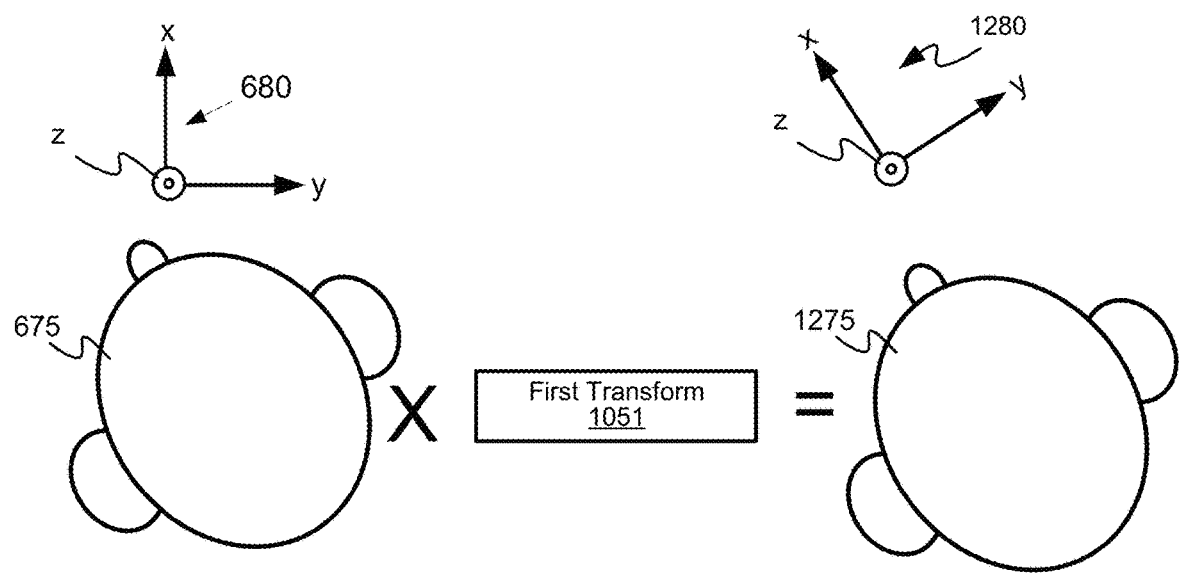

FIG. 12 depicts a transformation, using the first transform, of an anatomical magnetic resonance image to the patient anatomical magnetic resonance coordinate space, according to non-limiting examples.

Figure 13:
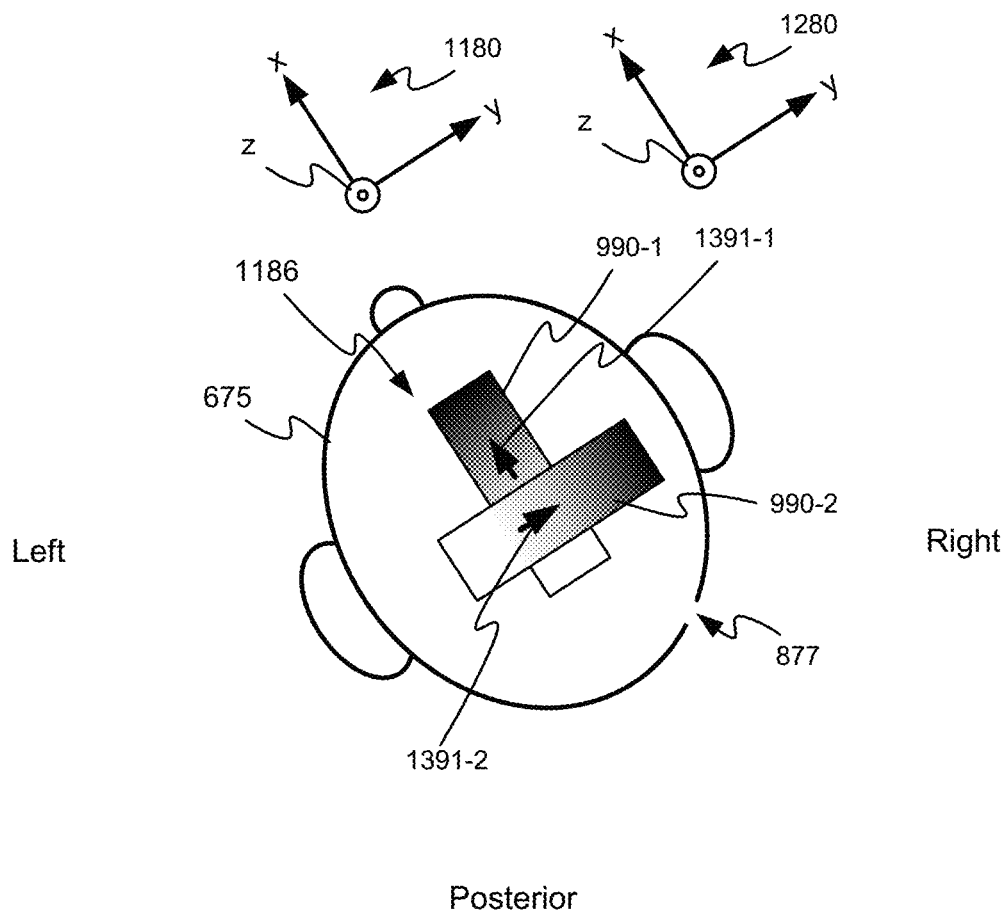

FIG. 13 depicts the diffusion-weighted magnetic resonance image, as transformed, overlaid on the anatomical magnetic resonance image, as transformed, according to non-limiting examples.

Figure 6:
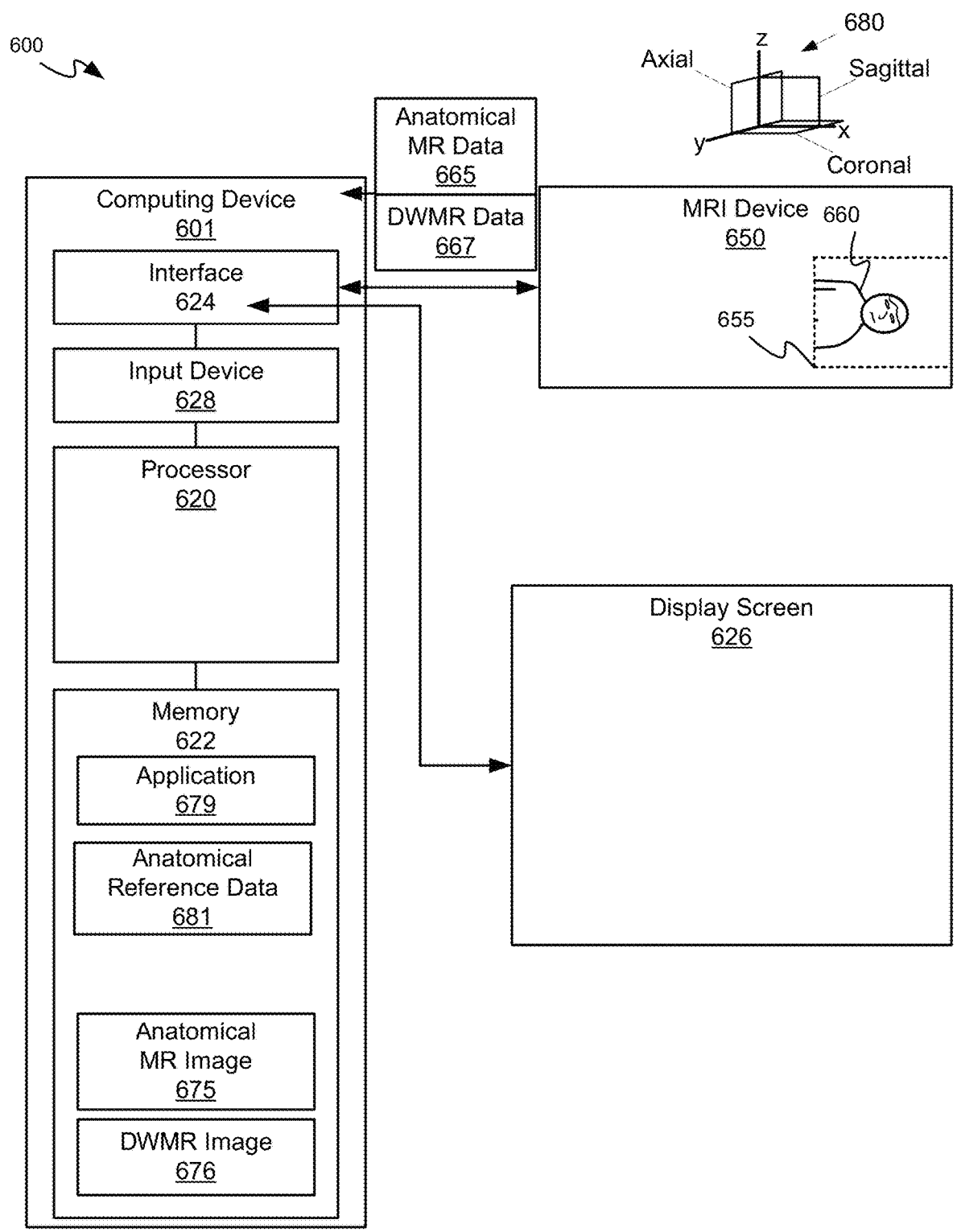
FIG. 6 depicts a medical imaging system and device for transforming a diffusion-weighted magnetic resonance image to a patient diffusion-weighted magnetic resonance coordinate space, according to non-limiting examples.
Figure 14:
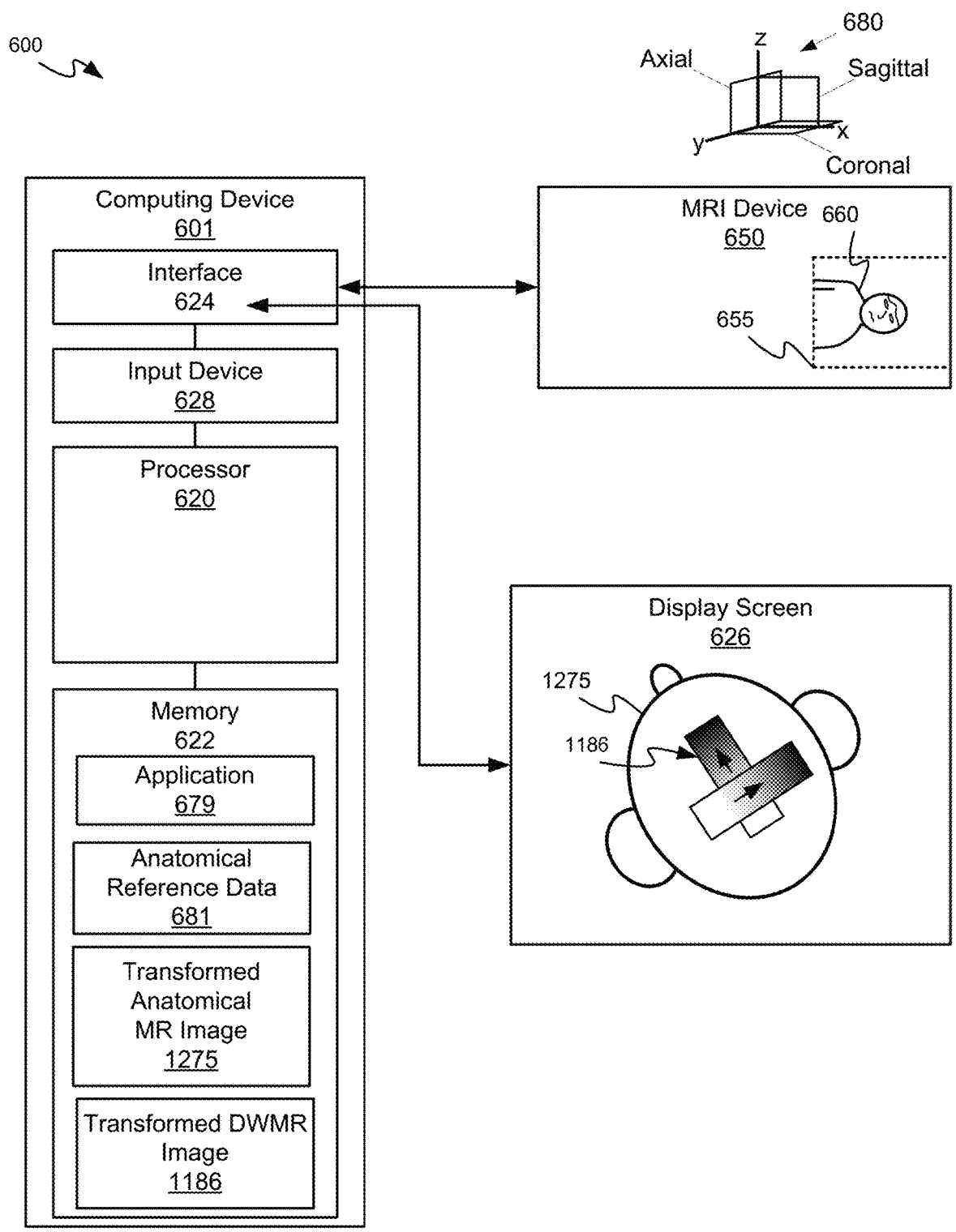

FIG. 14 depicts the system of FIG. 6 storing the diffusion-weighted magnetic resonance image, as transformed, and the anatomical magnetic resonance image, as transformed at one or more memories, as well as rendering the diffusion-weighted magnetic resonance image overlaid on the anatomical magnetic resonance image, as transformed, at a display screen, according to non-limiting examples.

Figure 15:
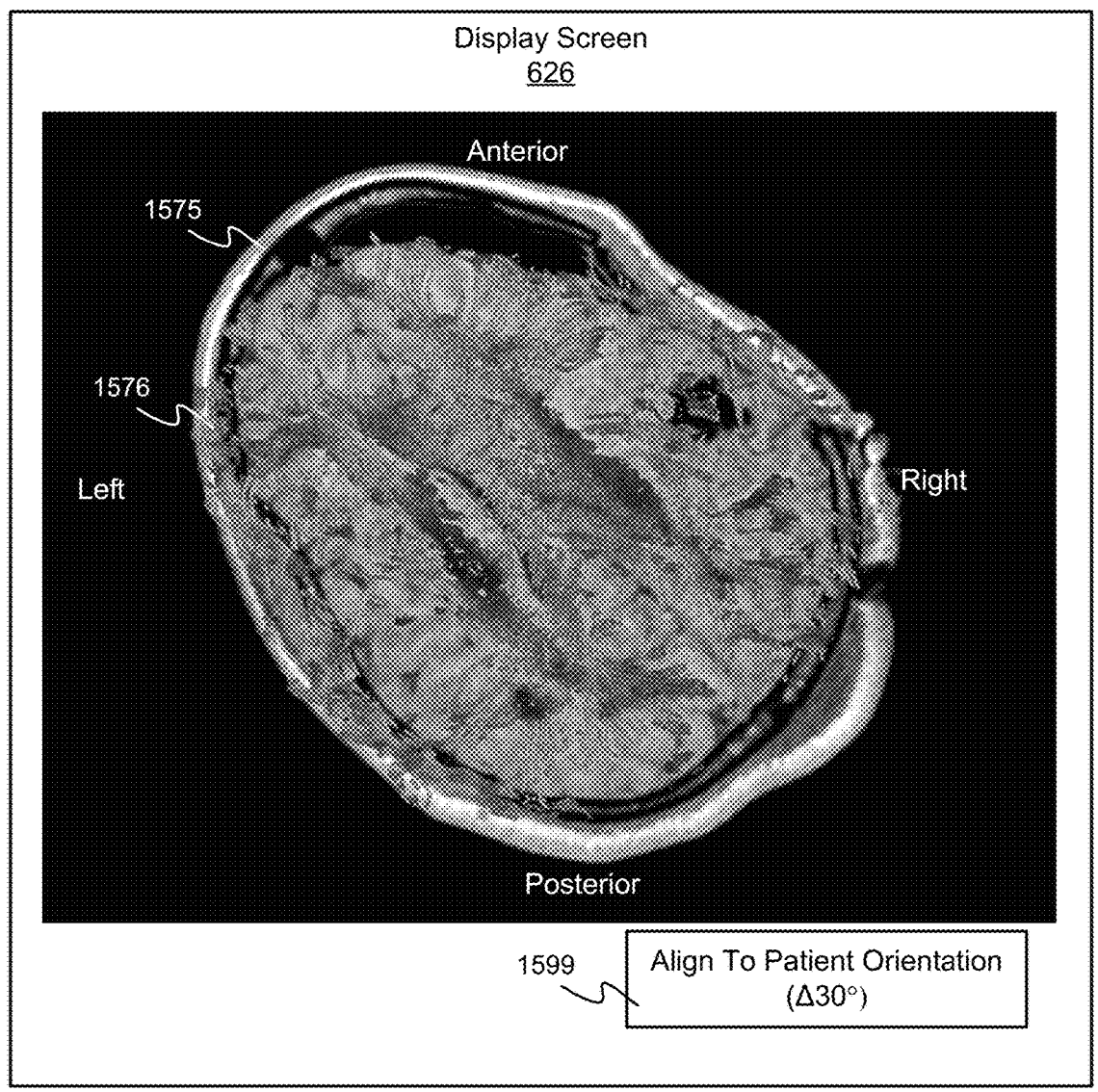

FIG. 15 depicts a color picture of a diffusion-weighted magnetic resonance image overlaid on an anatomical magnetic resonance image, according to non-limiting examples.

Figure 16:
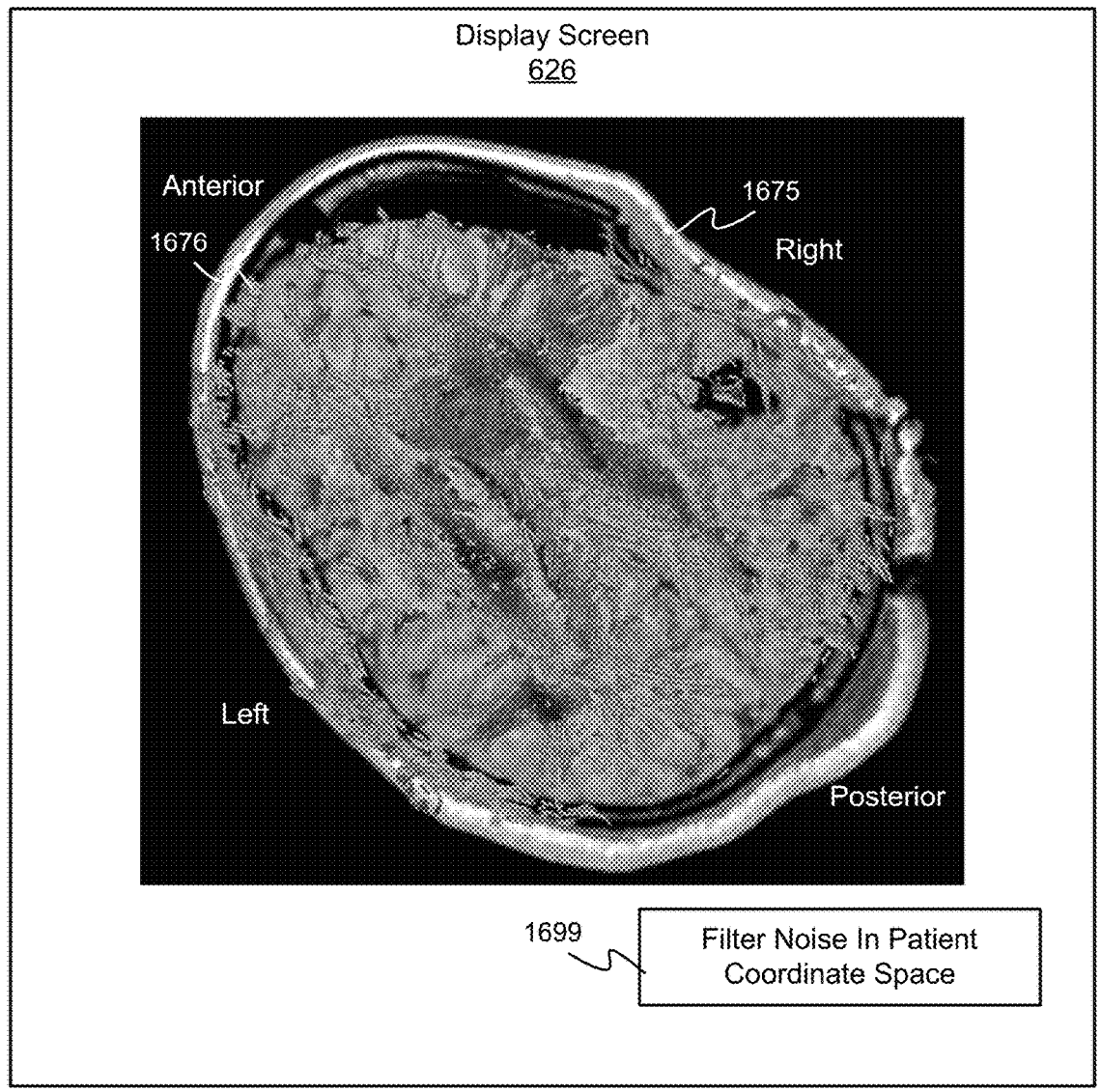

FIG. 16 depicts a color picture of a diffusion-weighted magnetic resonance image, as transformed, overlaid on an anatomical magnetic resonance image, as transformed, according to non-limiting examples.

DETAILED DESCRIPTION OF THE EMBODIMENTS

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

The present specification is directed to a medical imaging system for transforming a diffusion-weighted magnetic resonance image to a patient diffusion-weighted magnetic resonance coordinate space.

In particular, the present specification provides a device comprising: a processor in communication with a display screen and at least one memory, the at least one memory storing: an anatomical magnetic resonance (MR) image of a region of a patient; a diffusion-weighted magnetic resonance (DWMR) image of the region of the patient, the anatomical MR image and the DWMR image being in respective bore coordinate spaces associated with a bore of a magnetic resonance imaging device which acquired the anatomical MR image and the DWMR image of the region; and reference anatomical data associated with the region, the processor configured to: compare the anatomical MR image and the reference anatomical data to determine a first transform of a bore anatomical coordinate space of the anatomical MR image to a patient anatomical coordinate space associated with the patient; determine, from the first transform, a second transform of a bore DWMR coordinate space of the DWMR image to a patient DWMR coordinate space associated with the patient; transform, using the second transform, the DWMR image to the patient DWMR coordinate space; and control the display screen to render the DWMR image, as transformed, according to visual attributes associated with the patient DWMR coordinate space.

Figure 1:
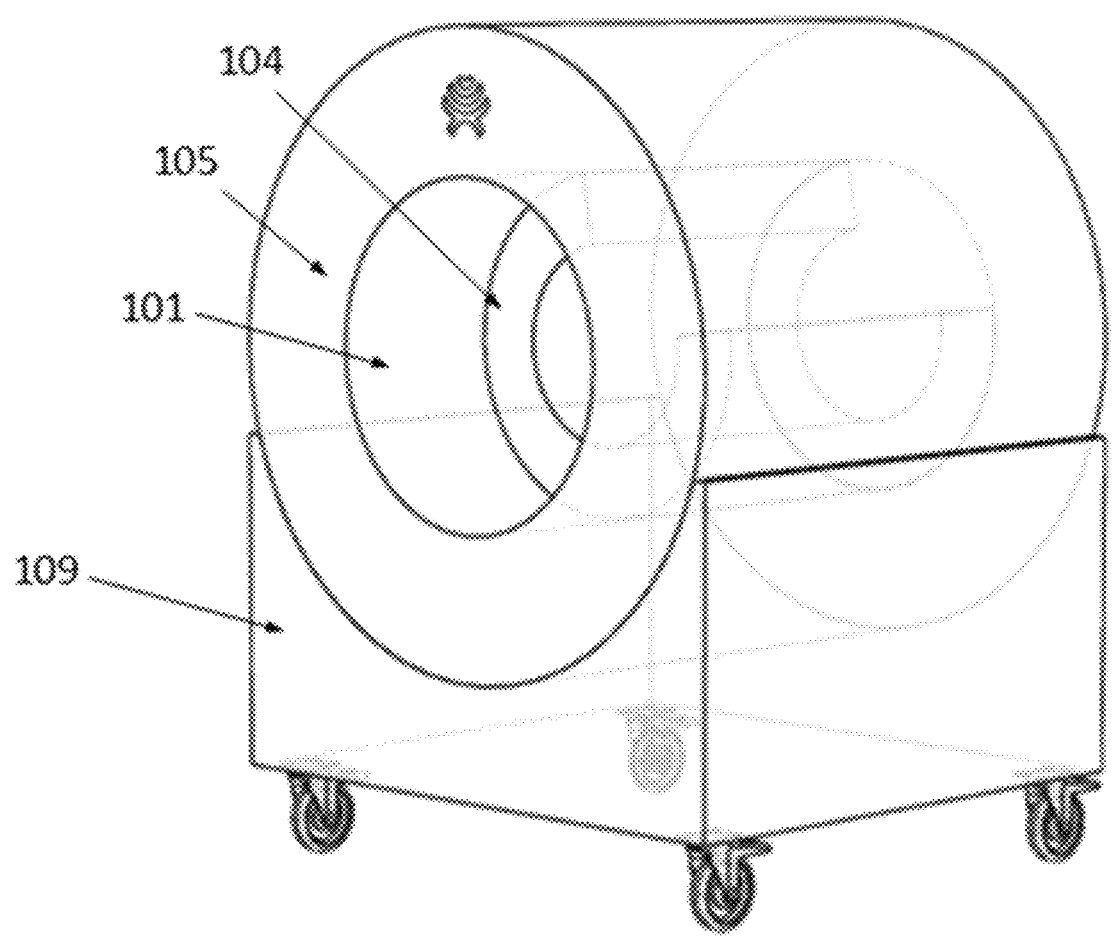
FIG. 1 shows a perspective view of an example of a magnetic resonance imaging (MRI) system.

The present specification further provides a method comprising: comparing, at a computing device, an anatomical magnetic resonance (MR) image of a region of a patient and reference anatomical data associated with the region to determine a first transform of a bore anatomical coordinate space of the anatomical MR image to a patient anatomical coordinate space associated with the patient; determining, at the computing device, from the first transform, a second transform of a bore diffusion-weighted magnetic resonance (DWMR) coordinate space of a DWMR image to a patient DWMR coordinate space associated with the patient, the anatomical MR image and the DWMR image being in respective bore coordinate spaces associated with a bore of a magnetic resonance imaging device which acquired the anatomical MR image and the DWMR image of the region; transforming, at the computing device, using the second transform, the DWMR image to the patient DWMR coordinate space; and controlling, using the computing device, a display screen to render the DWMR image, as transformed, according to visual attributes associated with the patient DWMR coordinate space Referring now to FIG. 1, an example of a magnetic resonance imaging (MRI) system 100 is shown in which a magnet housing 105 is placed on a base 109. Base 109 may include a portable cart, as shown. In some installations, base 109 may be affixed to the floor of the scanning room. Magnet housing 105 includes a solenoid magnet and bore area 101, where a human patient may be placed to be scanned. The solenoid magnet may be generally known as the main magnet. The solenoid magnet may generate a substantially uniform magnetic field for imaging the human patient placed inside bore area 101. This magnetic field may generally serve as a static polarizing field.

Figure 2:
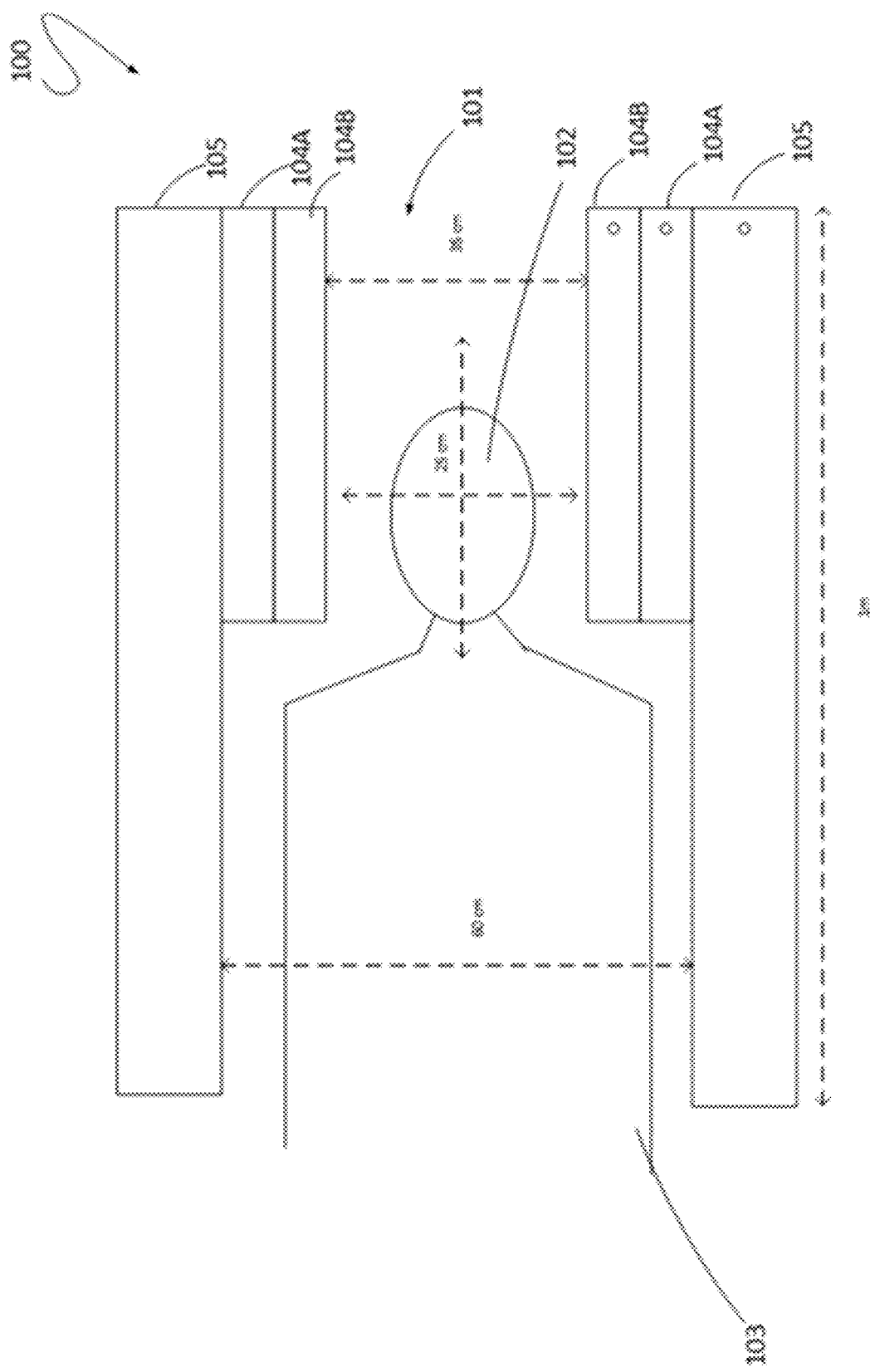
FIG. 2 shows a profile view of the MRI system.

Referring to FIG. 2, patient 103 may be placed in bore area 101. In this example, patient head area 102 is placed inside the magnetic field to be imaged by coil assembly 104. As shown in FIGS. 1 and 2, coil assembly 104 is shaped as an annular structure and housed within the inner bore of solenoid magnet. In this example, coil assembly 104 includes a gradient coil 104A and an RF coil 104B. The gradient coil 104A may generate a perturbation of the static polarizing field to encode magnetizations within the human patient's body. In some configurations, coil assembly 104 may include a radio frequency (RF) coil 104B to transmit RF pulses as excitation pulses. The RF coil 104B may also be configured to receive MR signals from the human patient in response to the RF pulses. In some instances, housing 105 may include separate receive coils to receive the MR signals from the human patient. In these instances, radio-frequency (RF) signals are, for example, transmitted by local coils for imaging a subject. In one example, a head coil in a birdcage configuration is used for both transmitting and receiving RF signals for imaging the subject's head area 102. In another instance, a surface coil is used for transmitting an RF signal into the subject and a phased array coil configuration is used for receiving MR signals in response.

Figure 3:
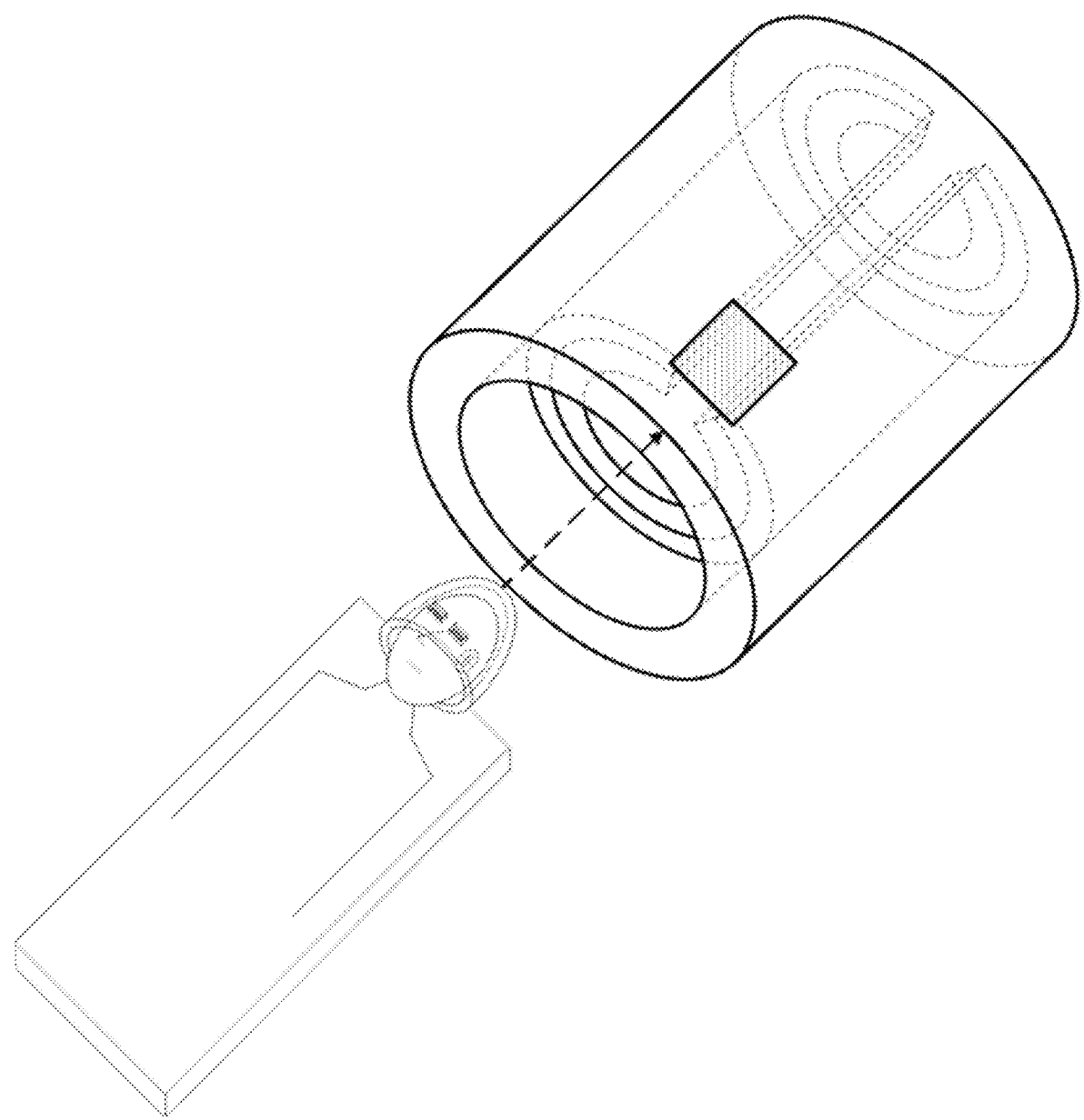
FIG. 3 shows an example embodiment illustrating the insertion of patient, wearing a head coil, into a magnetic resonance imaging system having a coil assembly with an aperture formed therein.

FIG. 3 shows an example embodiment illustrating the insertion of patient 160, supported by a table or stretcher 180, and wearing a head coil 230, into a magnetic resonance imaging system having a coil assembly with an aperture formed therein. In one instance, head coil 230 may be configured as a radio-frequency receiver coil as a local coil. In this instance, head coil 230 is configured to receive radio-frequency signals emitted from within the subject's head and in response to excitation radio frequency pulses sent from the transmit coil 130 within the annular coil assembly 135. In another instance, head coil 230 may be configured as a radio-frequency transmit and receiver coil. In the example embodiment shown, the aperture includes a display device, display screen and/or camera 252. The coil assembly and associated aperture may be rotatable to accommodate multiple patient orientations. The system includes an initial gap region 240 configured to accommodate the patient's shoulders and torso. The receiving coil may be positioned about the patient with the aperture as desired prior to installing them within the magnet. In this embodiment, the rotating coil assembly 135 includes the gradient coil 120 and transmitting coil 130.

Figure 4:
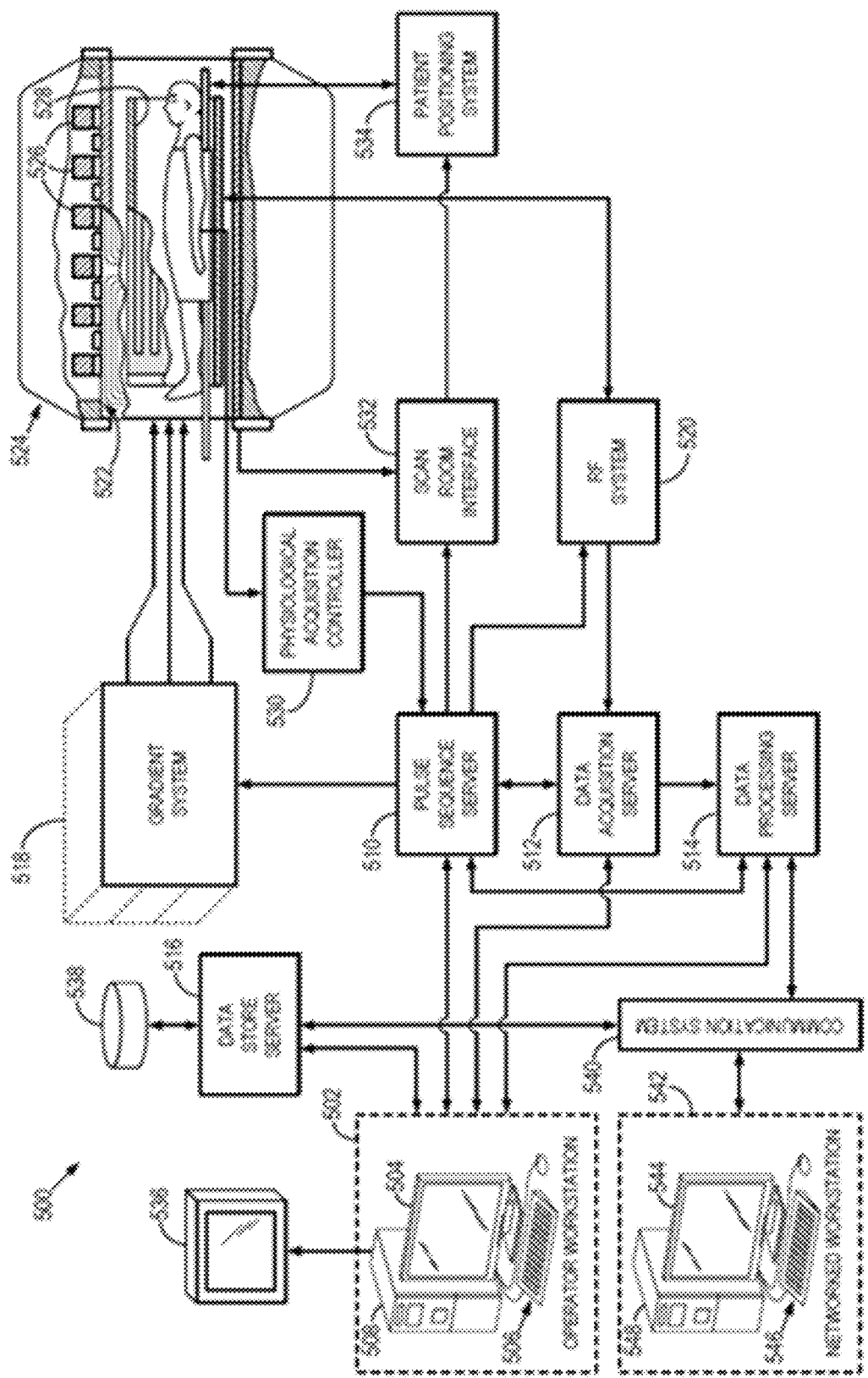
FIG. 4 is a block diagram of an example of an MRI system.

Referring particularly now to FIG. 4, an example of a magnetic resonance imaging ("MRI") system 500 is illustrated. The MRI system 500 includes an operator workstation 502, which will typically include a display 504; one or more input devices 506, such as a keyboard and mouse; and a processor 508. The processor 508 may include a commercially available programmable machine running a commercially available operating system. The operator workstation 502 provides the operator interface that enables scan prescriptions to be entered into the MRI system 500. In general, the operator workstation 502 may be coupled to four servers: a pulse sequence server 510; a data acquisition server 512; a data processing server 514; and a data store server 516. The operator workstation 502 and each server 510, 512, 514, and 516 are connected to communicate with each other. For example, the servers 510, 512, 514, and 516 may be connected via a communication system 540, which may include any suitable network connection, whether wired, wireless, or a combination of both. As an example, the communication system 540 may include both proprietary or dedicated networks, as well as open networks, such as the internet.

The pulse sequence server 510 functions in response to instructions downloaded from the operator workstation 502 to operate a gradient system 518 and a radiofrequency ("RF") system 520. Gradient waveforms necessary to perform the prescribed scan are produced and applied to the gradient system 518, which excites gradient coils in an assembly 522 to produce the magnetic field gradients $G_x$ $G_y$, and $G_z$ used for position encoding magnetic resonance signals. The gradient coil assembly 522 forms part of a magnet assembly 524 that includes a polarizing magnet 526 and a whole-body RF coil 528.

RF waveforms are applied by the RF system 520 to the RF coil 528, or a separate local coil (not shown in FIG. 4), in order to perform the prescribed magnetic resonance pulse sequence. Responsive magnetic resonance signals detected by the RF coil 528, or a separate local coil (not shown in FIG. 4), are received by the RF system 520, where they are amplified, demodulated, filtered, and digitized under direction of commands produced by the pulse sequence server 510. The RF system 520 includes an RF transmitter for producing a wide variety of RF pulses used in MRI pulse sequences. The RF transmitter is responsive to the scan prescription and direction from the pulse sequence server 510 to produce RF pulses of the desired frequency, phase, and pulse amplitude waveform. The generated RF pulses may be applied to the whole-body RF coil 528 or to one or more local coils or coil arrays (not shown in FIG. 4).

The RF system 520 also includes one or more RF receiver channels. Each RF receiver channel includes an RF preamplifier that amplifies the magnetic resonance signal received by the coil 528 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \qquad (1)$$

and the phase of the received magnetic resonance signal may also be determined according to the following relationship:

$$\varphi = \tan^{-1}\left(\frac{Q}{I}\right). \qquad (2)$$

The pulse sequence server 510 also optionally receives patient data from a physiological acquisition controller 530. By way of example, the physiological acquisition controller 530 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 510 to synchronize, or "gate," the performance of the scan with the subject's heart beat or respiration.

The pulse sequence server 510 also connects to a scan room interface circuit 532 that receives signals from various sensors associated with the condition of the patient and the magnet system. It is also through the scan room interface circuit 532 that a patient positioning system 534 receives commands to move the patient to desired positions during the scan.

The digitized magnetic resonance signal samples produced by the RF system 520 are received by the data acquisition server 512. The data acquisition server 512 operates in response to instructions downloaded from the operator workstation 502 to receive the real-time magnetic resonance data and provide buffer storage, such that no data is lost by data overrun. In some scans, the data acquisition server 512 does little more than pass the acquired magnetic resonance data to the data processor server 514. However, in scans that require information derived from acquired magnetic resonance data to control the further performance of the scan, the data acquisition server 512 is programmed to produce such information and convey it to the pulse sequence server 510. For example, during prescans, magnetic resonance data is acquired and used to calibrate the pulse sequence performed by the pulse sequence server 510. As another example, navigator signals may be acquired and used to adjust the operating parameters of the RF system 520 or the gradient system 518, or to control the view order in which k-space is sampled. In still another example, the data acquisition server 512 may also be employed to process magnetic resonance signals used to detect the arrival of a contrast agent in a magnetic resonance angiography ("MRA") scan. By way of example, the data acquisition server 512 acquires magnetic resonance data and processes it in real-time to produce information that is used to control the scan.

The data processing server 514 receives magnetic resonance data from the data acquisition server 512 and processes it in accordance with instructions downloaded from the operator workstation 502. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 514 are conveyed back to the operator workstation 502 where they are stored. Real-time images are stored in a data base memory cache (not shown in FIG. 4), from which they may be output to operator display 504 or a display 536 that is located near the magnet assembly 524 for use by attending physicians. Batch mode images or selected real time images are stored in a host database on disc storage 538. When such images have been reconstructed and transferred to storage, the data processing server 514 notifies the data store server 516 on the operator workstation 502. The operator workstation 502 may be used by an operator to archive the images, produce films, or send the images via a network to other facilities.

The MRI system 500 may also include one or more networked workstations 542. By way of example, a networked workstation 542 may include a display 544; one or more input devices 546, such as a keyboard and mouse; and a processor 548. The networked workstation 542 may be located within the same facility as the operator workstation 502, or in a different facility, such as a different healthcare institution or clinic.

The networked workstation 542, whether within the same facility or in a different facility as the operator workstation 502, may gain remote access to the data processing server 514 or data store server 516 via the communication system 540. Accordingly, multiple networked workstations 542 may have access to the data processing server 514 and the data store server 516. In this manner, magnetic resonance data, reconstructed images, or other data may be exchanged between the data processing server 514 or the data store server 516 and the networked workstations 542, such that the data or images may be remotely processed by a networked workstation 542. This data may be exchanged in any suitable format, such as in accordance with the transmission control protocol ("TCP"), the internet protocol ("IP"), or other known or suitable protocols.

Figure 5:
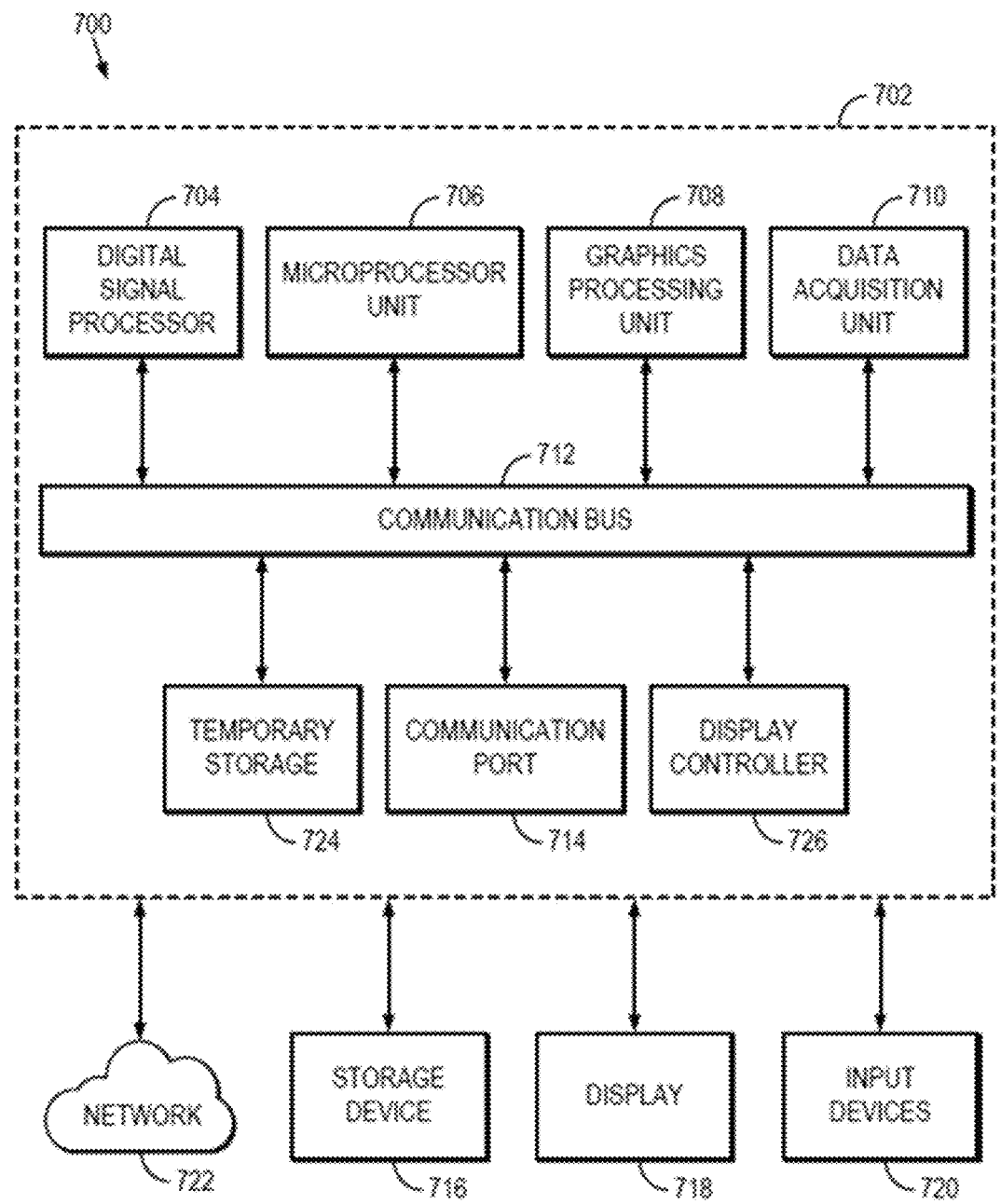
FIG. 5 is a block diagram of an example computer system that may be configured to implement the methods described herein.

Referring now to FIG. 5, a block diagram of an example computer system 700 that may be configured to co-register medical images acquired with different imaging modalities, as described above, is illustrated. The medical images to be co-registered may be provided to the computer system 700 from the respective medical imaging systems, such as an MRI system and a CT system, or from a data storage device, and are received in a processing unit 702.

In some embodiments, the processing unit 702 may include one or more processors. As an example, the processing unit 702 may include one or more of a digital signal processor ("DSP") 704, a microprocessor unit ("MPU") 706, and a graphics processing unit ("GPU") 708. The processing unit 702 may also include a data acquisition unit 710 that is configured to electronically receive data to be processed, which may include first and second medical images, image series, or image volumes. The DSP 704, MPU 706, GPU 708, and data acquisition unit 710 are all coupled to a communication bus 712. As an example, the communication bus 712 may be a group of wires, or a hardwire used for switching data between the peripherals or between any component in the processing unit 702.

The DSP 704 may be configured to receive and processes the first and second medical images. The MPU 706 and GPU 708 may also be configured to process the first and second medical images in conjunction with the DSP 704. As an example, the MPU 706 may be configured to control the operation of components in the processing unit 702 and may include instructions to perform processing of the first and second medical images on the DSP 704. Also as an example, the GPU 708 may process image graphics.

In some embodiments, the DSP 704 may be configured to process the first and second medical images received by the processing unit 702 in accordance with the algorithms described above. Thus, the DSP 704 may be configured to identify anatomical features in the images, to calculate registration parameters based on the identified anatomical features and known spatial relationships there between, and to co-register the images using the registration parameters.

The processing unit 702 preferably includes a communication port 714 in electronic communication with other devices, which may include a storage device 716, a display 718, and one or more input devices 720. Examples of an input device 720 include, but are not limited to, a keyboard, a mouse, and a touch screen through which a user may provide an input.

The storage device 716 is configured to store images, whether provided to or processed by the processing unit 702. The display 718 is used to display images, such as images that may be stored in the storage device 716, and other information. Thus, in some embodiments, the storage device 716 and the display 718 may be used for displaying the images before and after registration and for outputting other information, such as data plots or other reports based on the registration process.

The processing unit 702 may also be in electronic communication with a network 722 to transmit and receive data, including CT images, MR images, and other information. The communication port 714 may also be coupled to the processing unit 702 through a switched central resource, for example the communication bus 712.

The processing unit 702 may also include a temporary storage 724 and a display controller 726. As an example, the temporary storage 724 may store temporary information. For instance, the temporary storage 724 may be a random access memory.

Implementations relating to transforming a diffusion-weighted magnetic resonance image to a patient diffusion-weighted magnetic resonance coordinate space are next described which may be used within MRI devices and/or systems described herein.

In particular, it is understood that the MRI devices and/or systems described herein are configured to acquire magnetic resonance images of at least two types: anatomical MR images and diffusion-weighted magnetic resonance (DWMR) images. In particular, anatomical MR images comprise MR images that show an anatomy of a patient, and the like, imaged by an MRI imaging system; such anatomical MR images may include, but are not limited to T1-weighted images, T2-weighted images, and the like.

In contrast, DWMR images comprise images that show diffusion of water molecules in a patient, and the like, imaged by an MRI imaging system to generate contrast in MR images. DWMR images are generated from specific MRI sequences as well as software that generates images from the resulting data. DWMR images generally allows the mapping of the diffusion process of molecules, mainly water, in biological tissues and hence can show water pathways in the patient, which may correspond to neural pathways and the like. DWMR images may be overlaid and/or rendered with and/or on anatomical MR images such that the pathways mapped by the DWMR images are shown on the anatomy of a patient.

The anatomical MR images and the DWMR images are generally acquired and/or mapped in respective bore coordinate spaces associated with a bore of a magnetic resonance imaging device which acquired the anatomical MR images and the DWMR images. Indeed, as the anatomical MR images and the DWMR images are generally acquired using different MRI sequences, bore coordinate spaces of the anatomical MR images and the DWMR images are generally different from one another, though they may be generally aligned.

Furthermore, the pathways shown in the DWMR images are generally rendered with visual attributes that show pathways in each of three dimensions defined by a bore coordinate space, for example, coronal, axial, and sagittal planes (and/or X, Y, and Z directions and/or an x-axis, a y-axis and a z-axis) of the bore coordinate space.

The assumption in many MRI systems is that patient is generally aligned with the bore of the MRI device that acquired the images, and hence the visual attributes are generally meant to also show pathways in the patient in coronal, axial, and sagittal planes (and/or X, Y, and Z directions and/or an x-axis, a y-axis and a z-axis) of the patient. For example, when a head of a patient is being imaged, the intention is to show pathways from left to right in the patient (e.g. ear-to-ear) in a first color (and/or a first visual attribute), pathways from top to bottom of a patient (e.g. top of head-to-neck) in a second color (and/or a second visual attribute), and pathways from anterior to posterior of a patient (e.g. nose-to-back of head) in a third color (and/or a third visual attribute).

However, when the patient is not aligned with the bore coordinate space, the visual attributes of the DWRM images that are to show pathways in particular directions, may not properly show such pathways. For example, when the patient's head is tilted with respect to the bore, the visual attributes that are aligned with the coronal, axial, and sagittal planes (and/or X, Y, and Z directions and/or an x-axis, a y-axis and a z-axis) of the bore coordinate space are not generally aligned with the coronal, axial, and sagittal planes (and/or X, Y, and Z directions and/or an x-axis, a y-axis and a z-axis) of the patient. Examples of such alignment and misalignment are described below with respect to FIG. 8 and FIG. 9.

However, attention is next directed to FIG. 6, which depicts a medical imaging system 600 (interchangeably referred to hereafter as the system 600) for transforming a diffusion-weighted magnetic resonance image to a patient diffusion-weighted magnetic resonance coordinate space.

The system 600 generally comprises: a computing device 601 comprising a processor 620, at least one memory 622, and a communication interface 624; a display screen 626; an input device 628 configured to provide interactions with display screen 626; and an MRI device 650 configured to acquire anatomical MR images and DWMR images. For example, the MRI device 650 comprises a bore 655, into which a patient 660, and the like, may be positioned to perform imaging of the patient 660. While only a portion of the bore 655, and a head and shoulders of the patient 660 is depicted as being located in the bore 655, it is understood that the bore 655 may extend through the MRI device 650 and any region of the patient 660 located in any suitable area of the bore 655 may be imaged by the MRI device 650, as described with respect to FIG. 1 and FIG. 4.

In general, the anatomical MR image 675 and the DWMR image 676 are in respective bore coordinate spaces associated with the bore 655 of the MRI device 650 which acquired the anatomical MR image 675 and the DWMR image 676 of the region, which may lead to visual attributes of the DWMR image 676 being misaligned with a coordinate space of the patient. For example, as depicted, while the shoulders (e.g. and the body) of the patient 660 are aligned with the bore 655, the head of the patient 660 is turned with respect to the bore 655 and hence, visual attributes of the DWMR image 676, determined using a bore coordinate space, are generally misaligned with a coordinate space of the patient 660, as described in more detail below.

Furthermore, present examples will be described with respect to a head of the patient 660 being imaged. Hence, as described herein the anatomical MR image 675 and the DWMR image 676 are each of the head of the patient 660. However, it is understood that other regions of the patient 660 may be imaged (which may or may not include the head), and the anatomical MR image 675 and the DWMR image 676 may be of any suitable region of the patient 660. Furthermore, the anatomical MR image 675 and the DWMR image 676 are generally three-dimensional but may be two-dimensional, depending on settings of the MRI device 650 as controlled by the computing device 601.

In general, the anatomical MR image 675 and the DWMR image 676 are in respective bore coordinate spaces associated with the bore 655 of the MRI device 650 which acquired the anatomical MR image 675 and the DWMR image 676 of the region, which may lead to visual attributes of the DWMR image 676 being misaligned with a coordinate space of the patient. For example, as depicted, while the shoulders (e.g. and the body) of the patient 660 are aligned with the bore 655, the head of the patient 660 is turned with respect to the bore 655 and hence, visual attributes of the DWMR image 676, determined using a bore coordinate space, are generally misaligned with a coordinate space of the patient 660, as described in more detail below.

For example, the MRI device 650 is associated with a frame of reference and/or bore coordinate space 680 comprising an axial plane, a sagittal plane and a coronal plane, and/or a first axis (e.g. as depicted, the "x" axis), a second axis (e.g. as depicted, the "y" axis), and a third axis (e.g. as depicted, the "z" axis). Hereafter, for convenience, the first axis, the second axis, and the third axis of the bore coordinate space 680 will respectively be referred to as the x-axis, the y-axis and the z-axis.

As depicted, each of the planes and/or axes of the bore coordinate space 680 is defined with respect to the bore 655 of the MRI device 650. For example, the x-axis of the bore coordinate space 680 may be parallel to a longitudinal axis of the bore 655 and, for example, in an anterior/posterior direction; the y-axis of the bore coordinate space 680 may be perpendicular to the longitudinal axis of the bore 655, and, for example, in a left/right direction; and the z-axis of the bore coordinate space 680 may be perpendicular to x-axis and the y-axis (and the longitudinal axis of the bore 655), and, for example, in an up/down direction.

The system 600 may be generally configured to acquire digital MR images of patient 660 with the scanning oriented in the bore coordinate space 680. For example, magnetic gradients of the MRI device 650 are oriented with respect to the bore coordinate space 680; in other words, such magnetic gradients may be in a direction of the axial plane, the sagittal plane and the coronal plane and/or any of the x-axis, the y-axis and the z-axis.

However, as described above, the patient 660 need not be aligned with bore coordinate space 680. Indeed, as depicted, the patient 660 has been placed into a position where the head of the patient is rotated with respect to one or more of axes and/or planes of bore coordinate space 680. It will be assumed in present examples that the head of the patient 660 is rotated 30° with respect to the x-axis of the bore coordinate space 680, for example in a counterclockwise direction with respect to the z-axis of the bore coordinate space 680.

To assist with correcting the visual attributes of the DWMR image 676, the at least one memory 622 also stores reference anatomical data 681 associated with a region of the patient 660 that is imaged. For example, the reference anatomical data 681 may store attributes, and the like, of a human head, which may be compared with, for example, the anatomical MR image 675 to determine a first transform of a bore anatomical coordinate space of the anatomical MR image 675 to a patient anatomical coordinate space associated with the patient 660, as described in more detail below.

The computing device 601 may comprise one or more of the operator workstation 502, the networked workstation 542, depicted in FIG. 4, and the computer system 700, depicted in FIG. 5, with the processor 620, the at least one memory 622 and the communication interface 624 corresponding to suitable components of the operator workstation 502, the networked workstation 542, and/or the computer system 700; hence, while not depicted, the computing device 601 may also comprise other components such as one or more input devices. The display screen 626 may comprise a display device and/or a display screen of one or more of the operator workstation 502, the networked workstation 542, and/or the computer system 700, and may be integrated with the computing device 601 and/or comprise a stand-alone display device and/or a display screen, such as a monitor and the like. In particular, the display screen 626 may comprise any suitable one of or combination of CRT (cathode ray tube) and/or flat panel displays (e.g. LCD (liquid crystal display), plasma, OLED (organic light emitting diode), capacitive or resistive touch screens, and the like. In some examples, the display screen 626 comprises a touch screen, such that the display screen 626 comprises the input device 628.

Indeed, the input device 628 may comprise one or more of: a touchscreen at the display screen 626, a mouse, a rotatable mouse, a foot pedal, a microphone configured to receive voice commands, and a gesture-based input device. Other types of input devices will occur to persons of skill in the art and are within the scope of present examples.

The processor 620 may be implemented as a plurality of processors, including but not limited to one or more central processors (CPUs) and/or one or more processing units; either way, the processor 620 comprises a hardware element and/or a hardware processor of the computing device 601. The processor 620 is configured to communicate with the at least one memory 622 comprising a non-volatile storage unit (e.g. Erasable Electronic Programmable Read Only Memory ("EEPROM"), Flash Memory) and a volatile storage unit (e.g. random access memory ("RAM")). Furthermore, when the processor 620 is implemented as a plurality of processors, at least a first processor may be configured to communicate with the MRI device 650 using the interface 624, and at least a second processor may be configured to communicate with the display screen 626; the various processors may be in communication with each other. Programming instructions that implement the functional teachings of the computing device 601 as described herein are typically maintained, persistently, in the at least one memory 622 and used by the processor 620 which makes appropriate utilization of volatile storage during the execution of such programming instructions. Those skilled in the art recognize that the at least one memory the 622 is an example of computer readable media that may store programming instructions executable on the processor 620. Furthermore, the at least one memory 622 is also an example of a memory unit and/or memory module and/or a non-volatile memory and/or a non-transitory computer readable medium.

In particular, the at least one memory 622 stores an application 679 which, when executed by the processor 620, causes the processor 620 to: compare the anatomical MR image 675 and the reference anatomical data 681 to determine a first transform of a bore anatomical coordinate space of the anatomical MR image 675 to a patient anatomical coordinate space associated with the patient 660; determine, from the first transform, a second transform of a bore DWMR coordinate space of the DWMR image 676 to a patient DWMR coordinate space associated with the patient 660; transform, using the second transform, the DWMR image 676 to the patient DWMR coordinate space; and control the display screen 626 to render the DWMR image, as transformed, according to visual attributes associated with the patient DWMR coordinate space.

The application 679 may include, but is not limited to, any suitable machine learning algorithm, and the like, trained, for example, to determine the first transform of the bore anatomical coordinate space of the anatomical MR image 675 to the patient anatomical coordinate space associated with the patient 660 based on comparing anatomical MR images (e.g. similar to the anatomical MR image 675) and the reference anatomical data 681. However, the application 679 may also perform such functionality algorithmically.

Figure 7:
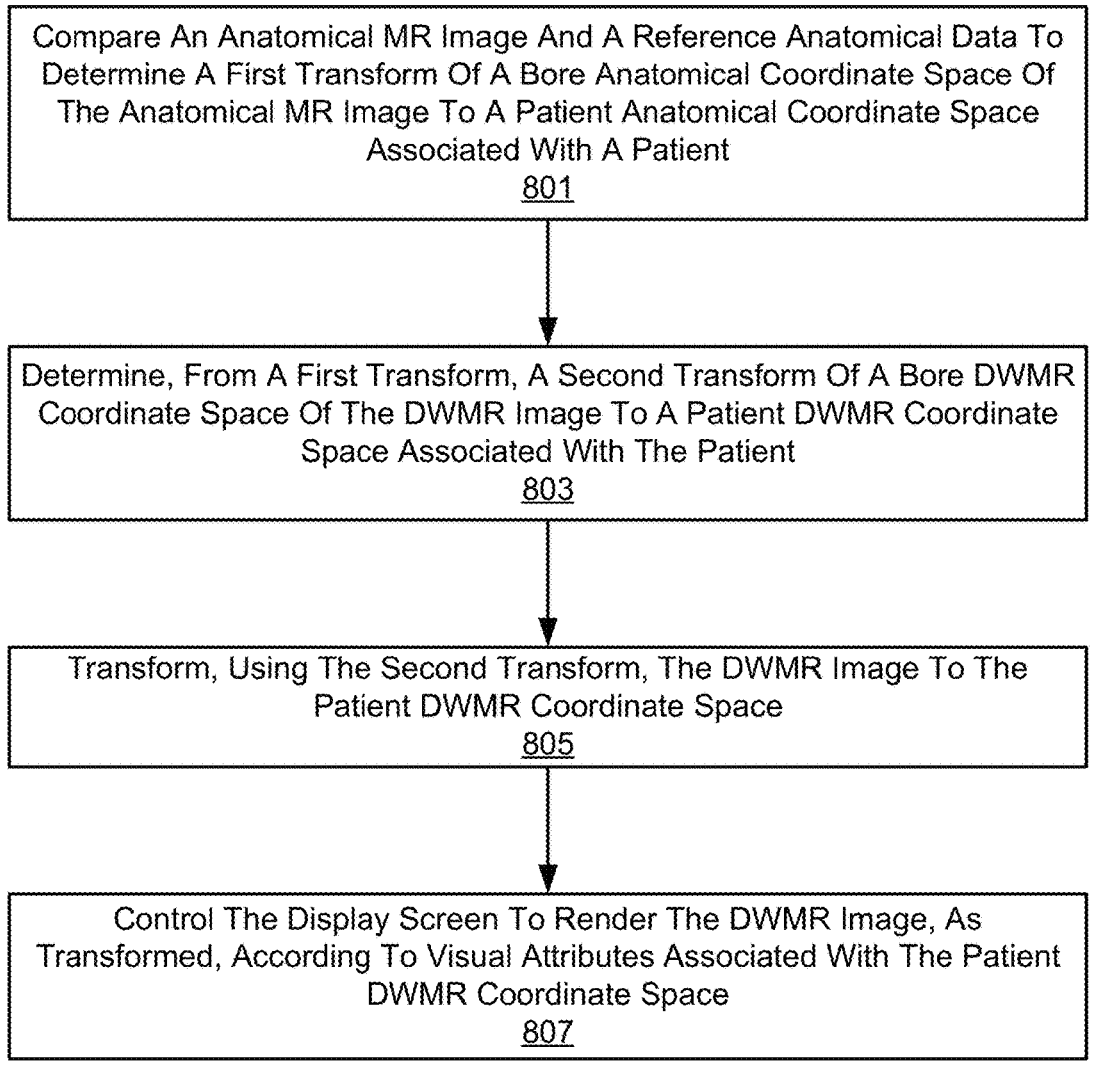
FIG. 7 depicts a method for transforming a diffusion-weighted magnetic resonance image to a patient diffusion-weighted magnetic resonance coordinate space, according to non-limiting examples.

Indeed, attention is now directed to FIG. 7 which depicts a flowchart of a method 800 for transforming a diffusion-weighted magnetic resonance image to a patient diffusion-weighted magnetic resonance coordinate space, according to non-limiting examples. In order to assist in the explanation of the method 800, it will be assumed that the method 800 is performed using the system 600, and specifically by the processor 620 of the computing device 601, for example when the processor 620 processes the application 679. Indeed, the method 800 is one way in which the computing device 601 may be configured. Furthermore, the following discussion of the method 800 will lead to a further understanding of the computing device 601, and the system 600 and its various components. However, it is to be understood that the system 600 and/or the method 800 may be varied, and need not work exactly as discussed herein in conjunction with each other, and that such variations are within the scope of present examples.

Regardless, it is to be emphasized, that the method 800 need not be performed in the exact sequence as shown, unless otherwise indicated; and likewise various blocks may be performed in parallel rather than in sequence; hence the elements of method 800 are referred to herein as "blocks" rather than "steps". It is also to be understood, however, that the method 800 may be implemented on variations of system 600 as well.

At block 801, the processor 620 compares the anatomical MR image 675 and the reference anatomical data 681 to determine a first transform of a bore anatomical coordinate space of the anatomical MR image 675 to a patient anatomical coordinate space associated with the patient 660.

For example, the processor 620 may be configured to determine the first transform by one or more of comparing and co-registering respective anatomical features of the anatomical MR image 675 and the reference anatomical data 681.

At block 803, the processor 620 determines, from the first transform, a second transform of a bore DWMR coordinate space of the DWMR image 676 to a patient DWMR coordinate space associated with the patient 660.

In some examples, at the block 805, the processor 620 may be further configured to filter DWMR data of the DWMR image 676 in the patient DWMR coordinate space, for example to remove extraneous data points and/or extreme data points (e.g. data points which may be outside the head of the patient 660 due to noise, and the like). In some of these examples, the processor 620 may be further configured to: control the display screen 626 to render a selectable option for filtering the DWMR data of the DWMR image 676 in the patient DWMR coordinate space; and when the selectable option is selected (e.g. via the input device 628), filter the DWMR data of the DWMR image 676 in the patient DWMR coordinate space. In this manner, the DWMR image 676 may be "cleaned up" automatically and/or upon receipt of input that selected the selectable option (e.g. manually).

At block 805, the processor 620 transforms, using the second transform, the DWMR image 676 to the patient DWMR coordinate space.

In some examples, at the block 805, the processor 620 be further configured to filter DWMR data of the DWMR image 676 in the patient DWMR coordinate space, for example to remove extraneous data points and/or extreme data points (e.g. data points which may be outside the head of the patient 660 due to noise, and the like). In some of these examples, the processor 620 may be further configured to: control the display screen 626 to render a selectable option for filtering the DWMR data of the DWMR image 676 in the patient DWMR coordinate space; and when the selectable option is selected (e.g. via the input device 628), filter the DWMR data of the DWMR image 676 in the patient DWMR coordinate space. In this manner, the DWMR image 676 may be "cleaned up" automatically and/or upon receipt of input that selected the selectable option (e.g. manually).

At block 807, the processor 620 controls the display screen to render the DWMR image 676, as transformed, according to visual attributes associated with the patient DWMR coordinate space.

In some examples, the processor 620 may be further configured to: store the DWMR image 676, as transformed, at the at least one memory 622.

Indeed, in further examples, the processor 620 may be further configured to: transform, using the first transform, the anatomical MR image 675 to the patient anatomical coordinate space; and store the anatomical MR image 675, as transformed, at the at least one memory 622.

The visual attributes may comprise one or more of: color attributes, greyscale attributes, line width attributes, transparency attributes, and the like. Hence, for example, neural pathways, and the like, in the head of the patient 660 may be represented with respect to color, greyscale, line widths, and/or transparency, and/or any other suitable visual attribute. Furthermore, the visual attributes may be rendered according to one or more of: a left and right of the DWMR image 676 as transformed to the patient DWMR coordinate space; a top and bottom of the DWMR image 676 as transformed to the patient DWMR coordinate space; and an anterior and posterior of the DWMR image 676 as transformed to the patient DWMR coordinate space.

An example of the method 800 is next described with respect to FIG. 8, FIG. 9, FIG. 10, FIG. 11, FIG. 12, FIG. 13, FIG. 14, FIG. 15 and FIG. 16.

Figure 8:
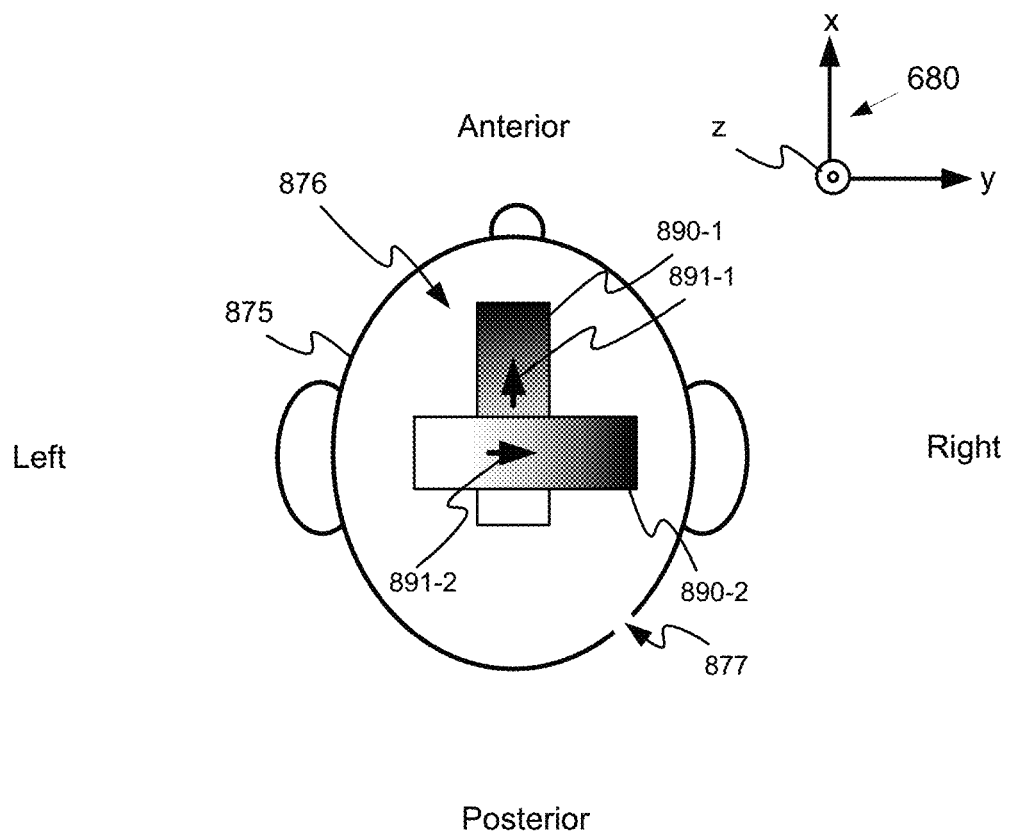
FIG. 8 depicts a diffusion-weighted magnetic resonance image overlaid on an anatomical magnetic resonance image of a head of a patient that is aligned with a bore of a magnetic resonance device, according to non-limiting examples.

Attention is next directed to FIG. 8 which depicts a highly simplified example of an anatomical MR image 875 and a DWMR image 876 of a head of the patient 660 when the head of the patient 660 is aligned with the bore 655 of the MRI device 650, which may be rendered at the display screen 626. As depicted, the DWMR image 876 is aligned with, and overlaid on, the anatomical MR image 875. In particular, the anatomical MR image 875 and the DWMR image 876 are each of a coronal slice of the head of the patient 660, for example in the coronal plane and/or the xy-plane of the bore coordinate space 680.

The x-axis and the y-axis of the bore coordinate space 680 is also depicted in FIG. 8, with the z-axis of the bore coordinate space 680 being "out" or "into" a page of FIG. 8. Also depicted are relative left, right, anterior and posterior directions of the bore coordinate space 680; as the head of the patient 660 is aligned with the bore 655, the relative left, right, anterior and posterior directions of the bore coordinate space 680 also apply to a coordinate space of the patient 660.

In particular, the anatomical MR image 875 and the DWMR image 876 may be provided in respective bore coordinate spaces. For example, the anatomical MR image 875 may be provided in a bore anatomical coordinate space, and the DWMR image 876 may be provided in a DWMR anatomical coordinate space. While each of the bore coordinate spaces of the anatomical MR image 875 and the DWMR image 876 may be generally aligned (and/or aligned with the bore coordinate space 680), the bore coordinate spaces of the anatomical MR image 875 and the DWMR image 876 may have different origins and/or have different axes and/or be of different coordinate system types as the anatomical MR image 875 and the DWMR image 876 are generally acquired using different MR sequences.

While the anatomical MR image 875 and the DWMR image 876 are depicted as two-dimensional, it is understood that the anatomical MR image 875 and the DWMR image 876 may be three-dimensional.

As depicted, the anatomical MR image 875 includes "head" anatomical features such as a cranium, ears and a nose. As depicted, the anatomical MR image 875 further includes a hole 877 which may be, for example, a corridor through which corridor based surgery on the brain of the patient 660 may occur and/or may be occurring. While not depicted, other "head" anatomical features may be in the anatomical MR image 875, such as a brain of the patient 660, and the like.

As depicted, the DWMR image 876 includes two diffusion pathways 890-1, 890-2 (interchangeably referred to hereafter, collectively, as the pathways 890 and, generically, as a pathway 890). Each pathway 890 represents water diffusion pathways of the patient 660. It is understood that the pathways 890 represent a highly simplified view of the DWMR image 876 and that real DWMR images include hundreds and/or thousands, etc., of smaller diffusion pathways than the two pathways 890 (for example see FIG. 15 and FIG. 16 described in more detail below).

Furthermore, while the pathways 890-1, 890-2 are respectively depicted in an x-direction and a y-direction (e.g. of the bore coordinate space 680), diffusion pathways in real DWMR images may be in any suitable direction. Similarly, while the pathways 890 are depicted as two-dimensional, it is understood that the pathways 890 may be three-dimensional.

Regardless of a direction of a pathway 890, each is provided (and/or rendered at the display screen 626) with one or more respective visual attributes showing a general trend of the pathways 890 with respect to the bore coordinate space 680.

For example, the pathway 890-1 has greyscale shading, as well as an arrow 891-1, in a direction of the x-axis of the bore coordinate space 680 (e.g. from posterior to anterior). Similarly, the pathway 890-2 has greyscale shading, as well as an arrow 891-2, in a direction of the y-axis of the bore coordinate space 680 (e.g. from left to right). While the visual attributes of the pathways 890 are depicted as two-dimensional, it is understood that the visual attributes of the pathways 890 may be three-dimensional.

In general, it is understood that the pathways 890 and the arrows 891 represent visual attributes of the DWMR image 876, which are different from anatomical features of the anatomical MR image 875. Indeed, the pathways 890 and the arrows 891 are shaded and/or colored and/or are in a particular direction, and the like, to show pathways, and the like, in the anatomical features but in a particular coordinate system, as depicted the bore coordinate space 680. In particular, the pathways 890 and the arrows 891 may follow and/or may be aligned with anatomical features, but do not represent the anatomical features themselves.

When the anatomical MR image 875 and the DWMR image 876 (including the pathways 890 and visual attributes thereof), are rendered at the display screen 626, a viewer is generally provided with a visual indication of the neural pathways in the head of the patient 660 with respect to the bore coordinate space 680. Put another way, the visual attributes of the pathways 890 generally show trends of the neural pathways with respect to the bore coordinate space 680. As the bore coordinate space 680 and a coordinate space of the patient 660 are aligned, the visual indication and/or the visual attributes and/or the trends of the neural pathways in the head of the patient 660 with respect to the bore coordinate space 680 rendered at the display screen 626 further provides a viewer with a visual indication of the neural pathways in the head of the patient 660 with respect to the patient 660.

However, when the head of the patient 660 is not aligned with the bore coordinate space 680, the visual attributes of the pathways 890 do not provide a viewer with a visual indication of the neural pathways in the head of the patient 660 with respect to the patient 660.

Figure 9:
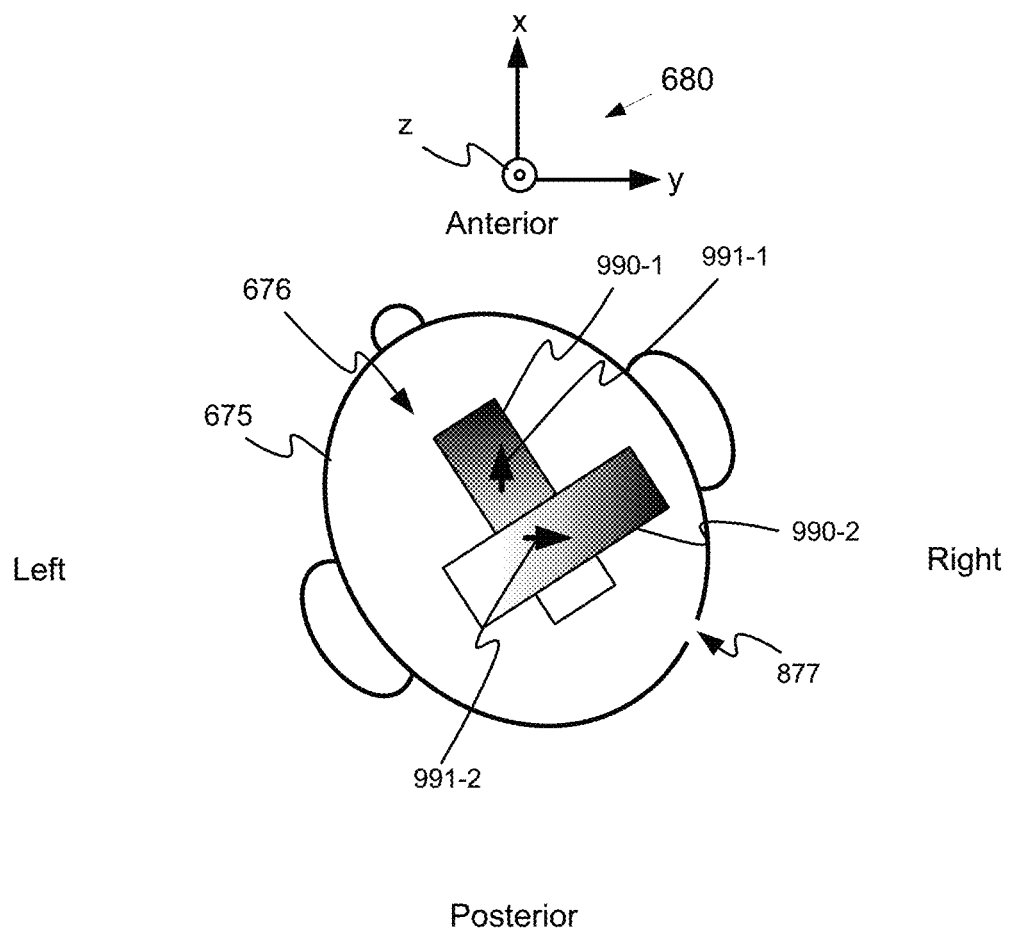
FIG. 9 depicts a diffusion-weighted magnetic resonance image overlaid on an anatomical magnetic resonance image of a head of a patient that is not aligned with a bore of a magnetic resonance device, according to non-limiting examples.

For example, attention is next directed to FIG. 9, which is substantially similar to FIG. 8, with like components having like numbers, but with the anatomical MR image 675 and the DWMR image 676 depicted, each in respective bore coordinate spaces similar to the anatomical MR image 875 and the DWMR image 876. As in FIG. 8 the anatomical MR image 675 and the DWMR image 676 may be rendered at the display screen 626, with the DWMR image 676 overlaid on the anatomical MR image 675.

In particular, as the head of the patient 660 depicted in FIG. 6 is rotated with respect to the bore 655 of the MRI device 650, the anatomical MR image 675 and the DWMR image 676 are not aligned with the bore coordinate space 680. Put another way, each of the anatomical MR image 675 and the DWMR image 676 are rotated with respect to the bore coordinate space 680, and similarly the anatomical MR image 675 and the DWMR image 676 are rotated, respectively, with respect to the anatomical MR image 875 and the DWMR image 876.

It is assumed in FIG. 9 that pathways 990-1, 990-2 (interchangeably referred to hereafter, collectively, as the pathways 990 and, generically, as a pathway 990) are respectively similar to the pathways 890-1, 890-2; however, similar to the anatomical MR image 675 and the DWMR image 676, the pathways 990 are also rotated with respect to the bore coordinate space 680 and/or the pathways 890.

Like the pathways 890, the pathways 990 are provided (and/or rendered at the display screen 626) with one or more respective visual attributes showing a general trend of the pathways 990 with respect to the bore coordinate space 680. For example, the pathway 990-1 has greyscale shading, as well as an arrow 991-1, in a direction of the x-axis of the bore coordinate space 680 (e.g. from posterior to anterior). Similarly, the pathway 990-2 has greyscale shading, as well as an arrow 991-2, in a direction of the y-axis of the bore coordinate space 680 (e.g. from left to right). When the anatomical MR image 675 and the DWMR image 676, with the pathways 990, are rendered at the display screen 626, the visual attributes of the pathways 990 provide an incorrect visual indication of the neural pathways in the head of the patient 660.

Again, in general, it is understood that the pathways 990 and the arrows 991 represent visual attributes of the DWMR image 676, which are different from anatomical features of the anatomical MR image 675. Indeed, the pathways 990 and the arrows 991 are shaded and/or colored and/or are in a particular direction, and the like, to show pathways, and the like, in the anatomical features but in a particular coordinate system, as depicted the bore coordinate space 680. In particular, the pathways 990 and the arrows 991 may follow and/or may be aligned with anatomical features, but do not represent the anatomical features themselves.

Attention is next directed to FIG. 10 which depicts an example of the block 801 and the block 803 of the method 800. While not depicted, it is understood that the example depicted in FIG. 10 is being implemented by the processor 620.

In particular, FIG. 10 depicts the anatomical MR image 675 being compared with the reference anatomical data 681. As depicted, the reference anatomical data 681 comprises data indicative of "head" anatomical features of humans, such as a cranium, ears, a nose, etc., for example in a coronal plane of the bore coordinate space 680. Such reference anatomical data 681 may represent "average" anatomical features of human beings, compiled, for example, by a standards body and/or as determined from a plurality of anatomical MR images of a plurality of human beings. The anatomical features of the reference anatomical data 681 need not be identical, however, to the anatomical features of the anatomical MR image 675; for example, as depicted, a cranium and nose of the reference anatomical data 681 is larger than the cranium and nose of the anatomical MR image 675. Similarly, the ears of the reference anatomical data 681 are smaller, and located farther forward, than the ears of the anatomical MR image 675. The reference anatomical data 681 is also lacking the hole 877.

While the reference anatomical data 681 is depicted visually and in two-dimensions, it is understood that the reference anatomical data 681 may be stored in a non-visual format (e.g. as machine learning classifiers, and the like) and/or in three-dimensions. In particular, as depicted, the reference anatomical data 681 may be provided with respect to the bore coordinate space 680, and/or the processor 620 may be configured to align the reference anatomical data 681 with the bore coordinate space 680.

The comparison of the anatomical MR image 675 and the reference anatomical data 681 may occur by comparing and/or co-registering anatomical features of the anatomical MR image 675 and the reference anatomical data 681. For example, a relative position of each of a nose, ears and cranium of each of the anatomical MR image 675 and the reference anatomical data 681 may occur. From such a comparison, it may be determined that the head of the patient 660, as represented by the anatomical MR image 675 is rotated with respect to the bore coordinate space 680.

From the comparison, the processor 620 determines (e.g. at the block 801), a first transform 1051 of a bore anatomical coordinate space (e.g. aligned with the bore coordinate space 680) of the anatomical MR image 675 to the patient anatomical coordinate space 1080 associated with the patient 660. For example, as depicted, the first transform 1051 may comprise data which, which applied to the bore anatomical coordinate space, causes the bore anatomical coordinate space to be rotated by 30°, with respect to the x-axis of the bore anatomical coordinate space, in a counterclockwise direction with respect to the z-axis of the bore anatomical coordinate space. In some examples, at least five features of the anatomical MR image 675 and the reference anatomical data 681 may be compared to determine the first transform 1051. In some examples, the first transform 1051 may be in a matrix format including, but not limited to, a 4×4 matrix.

From the first transform 1051, the processor 620 determines (e.g. at the block 803) a second transform 1052 of a bore DWMR coordinate space (e.g. aligned with the bore coordinate space 680) of the DWMR image 676 to a patient DWMR coordinate space associated with the patient 660. For example, as depicted, the second transform 1052 may comprise data which, which applied to the bore DWMR coordinate space (e.g. aligned with the bore coordinate space 680), causes the bore DWMR coordinate space to be rotated by 30° with respect to the x-axis of the bore DWMR coordinate space, in a counterclockwise direction with respect to the z-axis of the bore DWMR coordinate space. In some examples, the second transform 1052 may be in a matrix format including, but not limited to, a 4×4 matrix.

From the comparison, the processor 620 determines (e.g. at the block 801), a first transform 1051 of a bore anatomical coordinate space (e.g. aligned with the bore coordinate space 680) of the anatomical MR image 675 to the patient anatomical coordinate space 1080 associated with the patient 660. For example, as depicted, the first transform 1051 may comprise data which, which applied to the bore anatomical coordinate space, causes the bore anatomical coordinate space to be rotated by 30°, with respect to the x-axis of the bore anatomical coordinate space, in a counterclockwise direction with respect to the z-axis of the bore anatomical coordinate space. In some examples, at least five features of the anatomical MR image 675 and the reference anatomical data 681 may be compared to determine the first transform 1051. In some examples, the first transform 1051 may be in a matrix format including, but not limited to, a 4×4 matrix.

From the first transform 1051, the processor 620 determines (e.g. at the block 803) a second transform 1052 of a bore DWMR coordinate space (e.g. aligned with the bore coordinate space 680) of the DWMR image 676 to a patient DWMR coordinate space associated with the patient 660. For example, as depicted, the second transform 1052 may comprise data which, which applied to the bore DWMR coordinate space (e.g. aligned with the bore coordinate space 680), causes the bore DWMR coordinate space to be rotated by 30° with respect to the x-axis of the bore DWMR coordinate space, in a counterclockwise direction with respect to the z-axis of the bore DWMR coordinate space. In some examples, the second transform 1052 may be in a matrix format including, but not limited to, a 4×4 matrix.

Attention is next directed to FIG. 11 which depicts an example of the block 805 of the method 800. While not depicted, it is understood that the example depicted in FIG. 11 is being implemented by the processor 620.

In particular, in FIG. 11, the processor 620 transforms, using the second transform 1052, the DWMR image 676 to a patient DWMR coordinate space 1180. As such, coordinates of the DWMR image 676, for example in a bore DWMR coordinate space, are transformed to the patient DWMR coordinate space 1180 to produce, for example, a DWMR image 1186. As depicted, the visual attributes of the DWMR image 1186 are also redetermined, as described below with respect to FIG. 13.

In some examples, the processor 321 may be further configured to transform, using the first transform 1051, the anatomical MR image 675 to a patient anatomical coordinate space. For example, attention is next directed to FIG. 12 which depicts such a transformation of the anatomical MR image 675, in the bore coordinate space 680, to a patient anatomical coordinate space 1280, which may occur at any suitable place in the method 800 after the first transform 1051 is determined. In particular, in FIG. 12, the anatomical MR image 675 and a transformed MR image 1275 are depicted, along with the bore coordinate space 680 and the patient anatomical coordinate space 1280.

While not depicted, it is understood that the example of FIG. 12 is being implemented by the processor 620 and in particular the processor 620 is controlling the display screen 626 to render the transformed MR image 1275, as transformed to the patient anatomical coordinate space 1280. However, as no visual attributes of the transformed anatomical MR image 1275 are changed with respect to the anatomical MR image 675, the transformed anatomical MR image 1275 appears visually similar and/or the same as the anatomical MR image 675; rather coordinates of the anatomical MR image 675 are transformed from the bore coordinate space 680 to the patient anatomical coordinate space 1280 to produce the transformed anatomical MR image 1275.

Attention is next directed to FIG. 13 which depicts an example of the block 807 of the method 800, with FIG. 13 being substantially similar to FIG. 9 with like components having like numbers. In particular, in FIG. 13, the transformed anatomical MR image 1275 and the transformed DWMR image 1186 are depicted, as are the patient anatomical coordinate space 1280 and the patient DWMR coordinate space 1180.

As with the DWMR image 676 and the anatomical MR image 675 in FIG. 9, in FIG. 13 the transformed DWMR image 1186 is overlaid on the transformed anatomical MR image 1275.

While not depicted, it is understood that the example depicted in FIG. 13 is being implemented by the processor 620 and in particular the processor 620 is controlling the display screen 626 to render the DWMR image 1186, as transformed to the patient DWMR coordinate space 1180, according to visual attributes associated with the patient DWMR coordinate space 1180. As such, in contrast to the FIG. 9, where the visual attributes of the pathways 990 are rendered with respect to a bore DWMR coordinate space and/or the bore coordinate space 680, in FIG. 10, the visual attributes of the pathways 990 are rendered with respect to the patient DWMR coordinate space 1180.

For example, in FIG. 13, the pathways 990 are provided (and/or rendered at the display screen 626) with one or more respective visual attributes showing a general trend of the pathways 990 with respect to the patient DWMR coordinate space 1180. For example, the pathway 990-1 has greyscale shading, as well as an arrow 1391-1, in a direction of the x-axis of the patient DWMR coordinate space 1180 (e.g. from posterior to anterior of the head of the patient 660). Similarly, the pathway 990-2 has greyscale shading, as well as an arrow 1391-2, in a direction of the y-axis of the patient DWMR coordinate space 1180 (e.g. from left to right of the head of the patient 660). Hence, when the anatomical MR image 1275 and the transformed DWMR image 1186, with the pathways 990, are rendered at the display screen 626, the visual attributes of the pathways 990 provide a correct visual indication of the neural pathways in the head of the patient 660.

In some examples, the processor 620 may further store the DWMR image 1186, as transformed, at the at least one memory 622 and/or the processor 620 may further store the anatomical MR image 1275, as transformed, at the at least one memory 622. For example, attention is next directed to FIG. 14 which depicts the system 600 with the DWMR image 1186, as transformed, and the anatomical MR image 1275, as transformed, stored at the at least one memory 622. FIG. 14 further depicts the DWMR image 1186, as transformed, overlaid on the anatomical MR image 1275, as transformed, being rendered at the display screen 626, such that a viewer is provided with a visual indication of the neural pathways in the head of the patient 660 with respect to the patient DWMR coordinate space 1180.

As has been described previously, the MR images and DWMR images described heretofore are greatly simplified with respect to actual MR images and actual DWMR images. Hence, attention is next directed to FIG. 15 which depicts a color picture of an actual anatomical MR image 1575 (in a coronal plane) and an actual DWMR image 1576 (in the same coronal plane), overlaid on the anatomical MR image 1575, which, as depicted, are rendered at the display screen 626. The "Left", "Right", "Anterior" and "Posterior" directions of the bore coordinate space 680 are also depicted.

In contrast to the simplified DWMR image 676, the DWMR image 1576 comprises a plurality of pathways, which, as depicted, are color coded (e.g. have a visual attribute) that are provided with respect to the bore coordinate space 680. Hence, pathways of the DWMR image 1576 that tend to be in the anterior/posterior direction of the bore coordinate space 680 are depicted in green, pathways of the DWMR image 1576 that tend to be in the left/right direction of the bore coordinate space 680 are depicted in red, and, as the DWMR image 1576 is three-dimensional, pathways of the DWMR image 1576 that tend to be in the up/down direction (e.g. "out" or "into" a page of FIG. 15) of the bore coordinate space 680 are depicted in blue. Pathways may include more than one color (e.g. mixtures of one or more of red, green and blue), for example, when they tend in more than one of the aforementioned directions.

However, as the depicted head is tilted with respect to the bore coordinate space 680, the color coding of the pathways does not represent the direction of the pathways with respect to the patient 660; rather, the color coding of the pathways represent the direction of the pathways with respect to the bore coordinate space 680.

As such, the processor 620 may provide a selectable option 1599 which, when actuated and/or selected via the input device 628, causes the processor 620 to perform at least the block 805 and the block 807 of the method 800. As depicted, the selectable option 1599 includes text "Align To Patient Orientation (Δ30°)" which indicates that, when the selectable option 1599 is actuated and/or selected via the input device 628, the DWMR image 1576 will be transformed to a patient DWMR coordinate space (e.g. a patient orientation). Furthermore, the text "Δ30°" indicates that an orientation of the head of the patient 660 has been previously determined as being rotated 30° with respect to the bore coordinate space 680 (as described above) and hence the block 801 and the block 803 may already have been implemented, such that the first transform 1051 and the second transform 1052 have already been determined.

It is furthermore understood that the selectable option 1599 may be provided in a more complex system of menus rendered at the display screen 626, for example to one or more of: select which images to render, select various options for rendering the images (e.g. such as causing the DWMR image 1576 to be overlaid on the anatomical MR image 1575) filter noise in the bore coordinate space 680, and the like.

Attention is next directed to FIG. 16 which depicts a color picture of a transformed anatomical MR image 1675 and a transformed DWMR image 1676 (in the same coronal plane), overlaid on the transformed anatomical MR image 1675, which, as depicted, are rendered at the display screen 626. In particular, the transformed anatomical MR image 1675 and the transformed DWMR image 1676 are determined and rendered upon selection and/or actuation of the selectable option 1599.

Similar to the transformed MR image 1275 and the transformed DWMR image 1186, the transformed anatomical MR image 1675 and a transformed DWMR image 1676 are respectively determined from the first transform 1051 and the second transform 1052. Hence the transformed anatomical MR image 1675 is in the patient anatomical coordinate space 1280 and the transformed DWMR image 1676 is in the patient DWMR coordinate space 1280. The "Left", "Right", "Anterior" and "Posterior" directions of the patient coordinate spaces 1180, 1280 are also depicted.

The transformed anatomical MR image 1675 is similar to the anatomical MR image 1575. However, the pathways of the transformed DWMR image 1676 are color coded according to the patient DWMR coordinate space 1180. Indeed, the spatial locations of the pathways of the transformed anatomical MR image 1675 are the same and/or similar to the pathways of the anatomical MR image 1575, but the visual attributes (e.g. the color coding) is with respect to the patient DWMR coordinate space 1180 rather than the bore coordinate space 680.

Indeed, in general, the transformed DWMR image 1676 is similar to the DWMR image 1576, but transformed and/or color coded according to the patient DWMR coordinate space 1180. Indeed, the DWMR data of the DWMR image 1576 and the transformed DWMR image 1676 is the same, but transformed, in the transformed DWMR image 1676, from the bore coordinate space 680 to the patient DWMR coordinate space 1180.

As such, the pathways of the DWMR image 1676 that tend to be in the anterior/posterior direction of the bore coordinate space 680 are depicted in green, pathways of the DWMR image 1676 that tend to be in the left/right direction of the patient DWMR coordinate space 1180 are depicted in red, and, as the DWMR image 1676 is three-dimensional, pathways of the DWMR image 1676 that tend to be in the up/down direction e.g. "out" or "into" a page of FIG. 16) of the patient DWMR coordinate space 1180 are depicted in blue. Pathways may include more than one color (e.g. mixtures of one or more of red, green and blue), for example, when they tend in more than one of the aforementioned directions.

Also depicted in FIG. 16 is a selectable option 1699 which, when selected, causes the processor 620 to filter DWMR data of the DWMR image 1676, for example to remove outliers, noise, and the like. While not depicted, when the selectable option 1699 is actuated and/or selected (e.g. via the input device 628), the processor 620 filters DWMR data of the DWMR image 1676 in the patient DWMR coordinate space. In some examples, the selectable option 1699 may be part of a more complex menu system in which filtering parameters, and the like, may be selected, for example via sliders, and the like.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A device comprising:
a processor in communication with a display screen and at least one memory, the at least one memory storing:
an anatomical magnetic resonance (MR) image of a region of a patient;
a diffusion-weighted magnetic resonance (DWMR) image of the region of the patient, the anatomical MR image and the DWMR image being in respective bore coordinate spaces associated with a bore of a magnetic resonance imaging device which acquired the anatomical MR image and the DWMR image of the region, wherein the anatomical MR image is in a bore anatomical coordinate space and the DWMR image is in a bore DWMR coordinate space; and
reference anatomical data associated with the region, the processor configured to:
compare the anatomical MR image and the reference anatomical data to determine a first transform of the bore anatomical coordinate space of the anatomical MR image to a patient anatomical coordinate space associated with the patient, the first transform comprising data, which applied to the bore anatomical coordinate space, causes the bore anatomical coordinate space to be rotated a given angle to align the bore anatomical coordinate space with the patient anatomical coordinate space;
determine, from the first transform, a second transform of the bore DWMR coordinate space of the DWMR image to a patient DWMR coordinate space associated with the patient, the second transform comprising respective data, which applied to the bore DWMR coordinate space, causes the bore DWMR coordinate space to be rotated by the given angle to align the bore DWMR coordinate space with the patient DWMR coordinate space, wherein the first transform and the second transform are in matrix format;
transform, using the second transform, the DWMR image to the patient DWMR coordinate space;
determine visual attributes associated with the patient DWMR coordinate space, the visual attributes comprising one or more of: color attributes, greyscale attributes, line width attributes, and transparency attributes; and
control the display screen to render the DWMR image, as transformed, according to the visual attributes associated with the patient DWMR coordinate space,
wherein the visual attributes associated with the patient DWMR coordinate space represent a plurality of pathways and are rendered according to:
first visual attribute according to a left and right of the DWMR s transformed to a first pathway in the patient DWMR coordinate space;
second visual attribute according to a top and bottom of the DWMR image as transformed to a second pathway in the patient DWMR coordinate space; and
third visual attribute according to an anterior and posterior of the DWMR image as transformed to a third pathway in the patient DWMR coordinate space.

2. The device of claim 1, wherein the processor is further configured to:
determine the first transform by one or more of comparing and co-registering respective anatomical features of the anatomical MR image and the reference anatomical data.

3. The device of claim 1, wherein the processor is further configured to:
control the display screen to render a selectable option for transforming at least the DWMR image to the patient DWMR coordinate space; and
when the selectable option is selected, determine the second transform, transform, the DWMR image to the patient DWMR coordinate space, and control the display screen to render the DWMR image according to the visual attributes associated with the patient DWMR coordinate space.

4. The device of claim 3, wherein the processor is further configured to one or more of:
determine the first transform before the selectable option is selected; and
determine the first transform after the selectable option is selected.

5. The device of claim 1, wherein the processor is further configured to:
filter DWMR data of the DWMR image in the patient DWMR coordinate space.

6. The device of claim 5, wherein the processor is further configured to:
control the display screen to render a selectable option for filtering the DWMR data of the DWMR image in the patient DWMR coordinate space; and
when the selectable option is selected, filter the DWMR data of the DWMR image in the patient DWMR coordinate space.

7. The device of claim 1, wherein the processor is further configured to:
transform, using the first transform, the anatomical MR image to the patient anatomical coordinate space; and
store the anatomical MR image, as transformed, at the at least one memory.

8. The device of claim 1, wherein the processor is further configured to:
store the DWMR image, as transformed, at the at least one memory.

9. A method comprising:
comparing, at a computing device, an anatomical magnetic resonance (MR) image of a region of a patient and reference anatomical data associated with the region to determine a first transform of a bore anatomical coordinate space of the anatomical MR image to a patient anatomical coordinate space associated with the patient, the first transform comprising data, which applied to the bore anatomical coordinate space, causes the bore anatomical coordinate space to be rotated a given angle to align the bore anatomical coordinate space with the patient anatomical coordinate space;

determining, at the computing device, from the first transform, a second transform of a bore diffusion-weighted magnetic resonance (DWMR) coordinate space of a DWMR image to a patient DWMR coordinate space associated with the patient, the anatomical MR image and the DWMR image being in respective bore coordinate spaces associated with a bore of a magnetic resonance imaging device which acquired the anatomical MR image and the DWMR image of the region, the second transform comprising respective data, which applied to the bore DWMR coordinate space, causes the bore DWMR coordinate space to be rotated by the given angle to align the bore DWMR coordinate space with the patient DWMR coordinate space wherein the first transform and the second transform are in matrix format;

transforming, at the computing device, using the second transform, the DWMR image to the patient DWMR coordinate space;

determining visual attributes associated with the patient DWMR coordinate space, the visual attributes comprising one or more of: color attributes, greyscale attributes, line width attributes, and transparency attributes; and controlling, using the computing device, a display screen to render the DWMR image, as transformed, according to the visual attributes associated with the patient DWMR coordinate space, wherein the visual attributes associated with the patient DWMR coordinate space represent a plurality of pathways and are rendered according to:
first visual attribute according to a left and right of the DWMR s transformed to a first pathway in the patient DWMR coordinate space;
second visual attribute according to a top and bottom of the DWMR image as transformed to a second pathway in the patient DWMR coordinate space; and
third visual attribute according to an anterior and posterior of the DWMR image as transformed to a third pathway in the patient DWMR coordinate space.

10. The method of claim 9, further comprising:
determining the first transform by one or more of comparing and co-registering respective anatomical features of the anatomical MR image and the reference anatomical data.

11. The method of claim 9, further comprising:
controlling the display screen to render a selectable option for transforming at least the DWMR image to the patient DWMR coordinate space; and
when the selectable option is selected, determine the second transform, transforming, the DWMR image to the patient DWMR coordinate space, and control the display screen to render the DWMR image according to the visual attributes associated with the patient DWMR coordinate space.

12. The method of claim 11, further comprising one or more of:
determining the first transform before the selectable option is selected; and
determining the first transform after the selectable option is selected.

13. The method of claim 9, further comprising:
filtering DWMR data of the DWMR image in the patient DWMR coordinate space.

14. The method of claim 13, further comprising:
controlling the display screen to render a selectable option for filtering the DWMR data of the DWMR image in the patient DWMR coordinate space; and
when the selectable option is selected, filtering the DWMR data of the DWMR image in the patient DWMR coordinate space.

15. The method of claim 9, further comprising:
transforming, using the first transform, the anatomical MR image to the patient anatomical coordinate space; and
storing the anatomical MR image, as transformed, at a memory.

16. The method of claim 9, further comprising:
storing the DWMR image, as transformed, at a memory.

* * * * *